US010621700B1

(12) United States Patent
Holmes et al.

(10) Patent No.: US 10,621,700 B1
(45) Date of Patent: Apr. 14, 2020

(54) COMPUTED RADIOGRAPHY CONTRAST, NOISE AND RESOLUTION IMPROVEMENT

(71) Applicant: Lickenbrock Technologies LLC, St. Louis, MO (US)

(72) Inventors: Timothy Holmes, St. Louis, MO (US); Melena Abijaoude, St. Louis, MO (US); Sean Larkin, St. Louis, MO (US); John Peters, St. Louis, MO (US); Lukas Kirchner, Baltimore, MD (US)

(73) Assignee: Lickenbrock Technologies LLC, St. Louis, MO (US)

( * ) Notice: Subject to any disclaimer, the term of this patent is extended or adjusted under 35 U.S.C. 154(b) by 153 days.

(21) Appl. No.: 16/007,231

(22) Filed: Jun. 13, 2018

Related U.S. Application Data

(60) Provisional application No. 62/523,013, filed on Jun. 21, 2017.

(51) Int. Cl.
*G06K 9/00* (2006.01)
*G06T 5/00* (2006.01)
(Continued)

(52) U.S. Cl.
CPC ............ *G06T 5/002* (2013.01); *G06K 9/6215* (2013.01); *G06T 5/50* (2013.01); *G06T 7/0014* (2013.01); *G16H 30/40* (2018.01); *G06K 2209/05* (2013.01); *G06T 2207/10116* (2013.01); *G06T 2207/20104* (2013.01); *G06T 2207/20221* (2013.01)

(58) Field of Classification Search
CPC ......... G06T 5/002; G06T 5/007; G06T 5/008; G06T 5/009; G06T 5/50; G06T 7/0012;
(Continued)

(56) References Cited

U.S. PATENT DOCUMENTS 6,628,749 B2    9/2003    Wei et al.
7,692,161 B2    4/2010    Corby, Jr. et al.
(Continued)

FOREIGN PATENT DOCUMENTS

WO      03030104 A1      4/2003

OTHER PUBLICATIONS

Schnell, Erich A. et al.; "Plate-specific gain map correction for the improvement of detective quantum efficiency in computed radiography"; Med. Phys. 39 (3); Mar. 2012; Published Feb. 27, 2012; Copyright 2012 Am. Assoc. Phys. Med.; pp. 1495-1504.
(Continued)

*Primary Examiner* — Jose L Couso
(74) *Attorney, Agent, or Firm* — Hoffman Warnick LLC

(57) ABSTRACT

A system, method and program product for enhancing radiographic images. A disclosed method includes: determining a sensitivity function of a computed radiography (CR) plate from at least one blank plate image, wherein the sensitivity function is a measure of noise caused by a phosphor grain pattern in the CR plate; inputting a specimen image captured using the CR plate; generating a blank plate-to-specimen (B2S) alignment map that provides a correspondence between pixel locations in the sensitivity function and the specimen image; applying a sensitivity function correction algorithm to the specimen image based on the B2S alignment map, wherein the sensitivity function correction algorithm is derived from the sensitivity function; and outputting an enhanced specimen image. A second disclosed method includes merging independent images of the same specimen to reduce noise. A third disclosed method includes a deconvolution algorithm for improving spatial resolving power.

28 Claims, 16 Drawing Sheets

(51) Int. Cl.
*G16H 30/40* (2018.01)
*G06T 5/50* (2006.01)
*G06K 9/62* (2006.01)
*G06T 7/00* (2017.01)

(58) Field of Classification Search
CPC ......... G06T 7/0014; G06T 2207/10116; G06T 2207/20104; G06T 2207/20221; G06K 2209/05; G06K 9/6215; G16H 30/40; G03C 5/16; A61B 6/508; A61B 6/4216; G02B 26/10; G03B 42/08; G03B 42/02; H04N 1/02895; H04N 1/407; H04N 1/6088; H04N 2201/0458; H04N 2201/3242; G01T 1/2012; G12K 2004/06; G12K 2004/04; H05G 1/60
See application file for complete search history.

(56) References Cited

U.S. PATENT DOCUMENTS

| | | | | |
|---|---|---|---|---|
| 2004/0258201 | A1* | 12/2004 | Hayashida | A61B 6/583 378/62 |
| 2013/0287281 | A1* | 10/2013 | Cresens | G06T 5/00 382/132 |

OTHER PUBLICATIONS

De Almeida, Gevaldo L. et al.; "A Novel Algorithm for Blind Deconvolution Applied to The Improvement of Radiographic Images"; XXXV Brazilian Workshop on Nuclear Physics; AIP Conf. Proc. 1529; 2013; Copyright 2013 AIP Publishing LLC; pp. 95-99.

Ewert, K. Heyne et al.; "Optimum Exposure Conditions for Computed Radiography Depending on Fixed Pattern Noise and Efficiency of Imaging Plate-Scanner Systems"; Review of Progress in Quantitative Nondestructive Evaluation; vol. 30; AIP Conf. Proc. 1335; 2011; Copyright 2011 American Institute of Physics; pp. 493-500.

Sanchez, Guadalupe et al.; "Estimated Radiation Dose Reduction Using Non-Linear Diffusion Method in Computed Radiography"; 34th Annual International Conference of the IEEE EMBS; San Diego, California; Aug. 28-Sep. 1, 2012; Copyright 2012 IEEE; pp. 1502-1505.

Sivakumar, Janaki et al.; "Computed Radiography Skull Image Enhancement Using Wiener Filter"; Proceedings of the International Conference on Pattern Recognition, Informatics and Medical Engineering; Mar. 21-23, 2012; copyright 2012 IEEE; pp. 5.

* cited by examiner

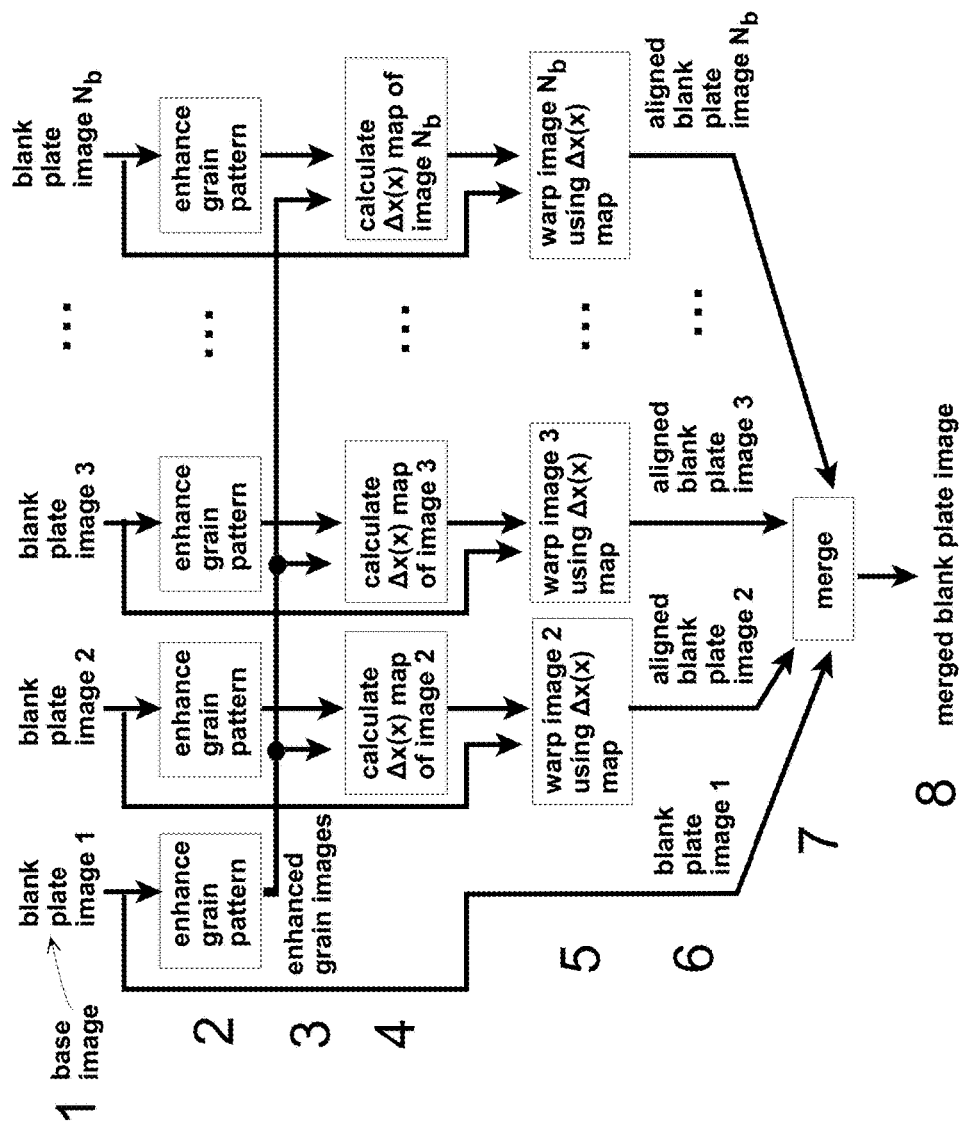
Figure 3: Process flow for merging blank plate images.

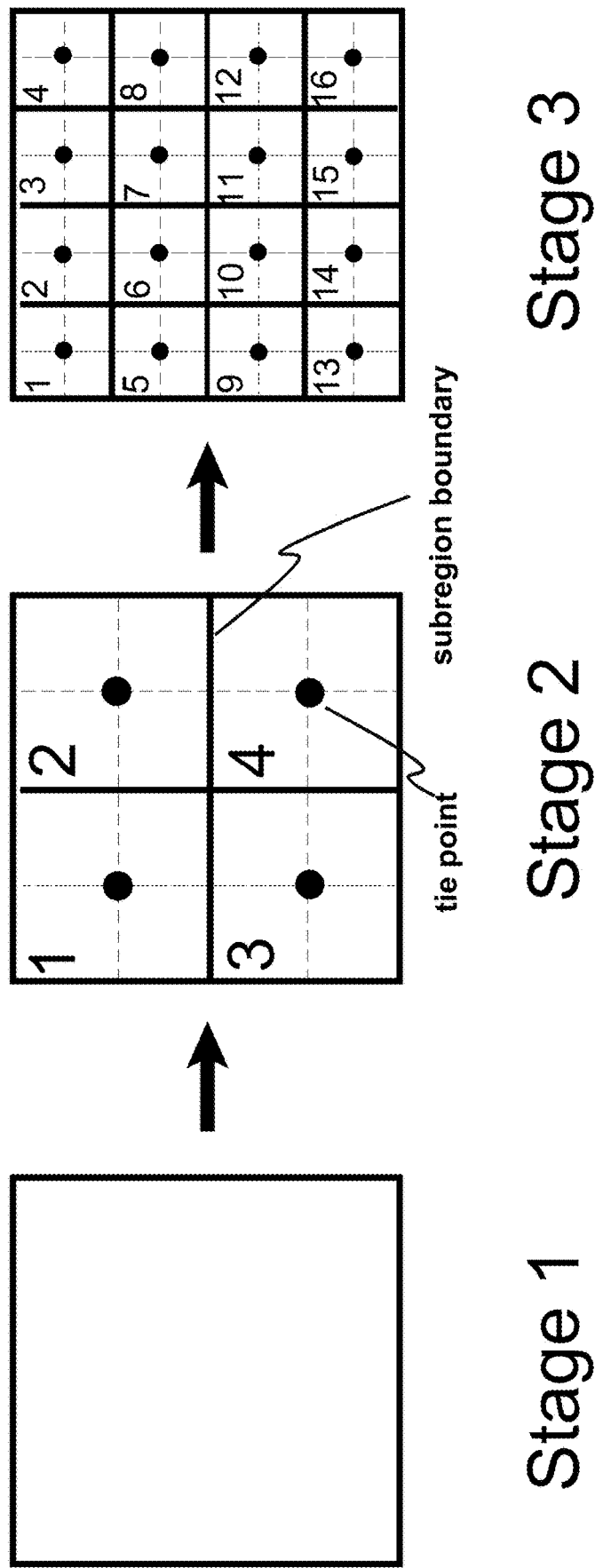
Figure 4: Depiction of the progressive decomposition of subregions used for alignment with geometric distortion

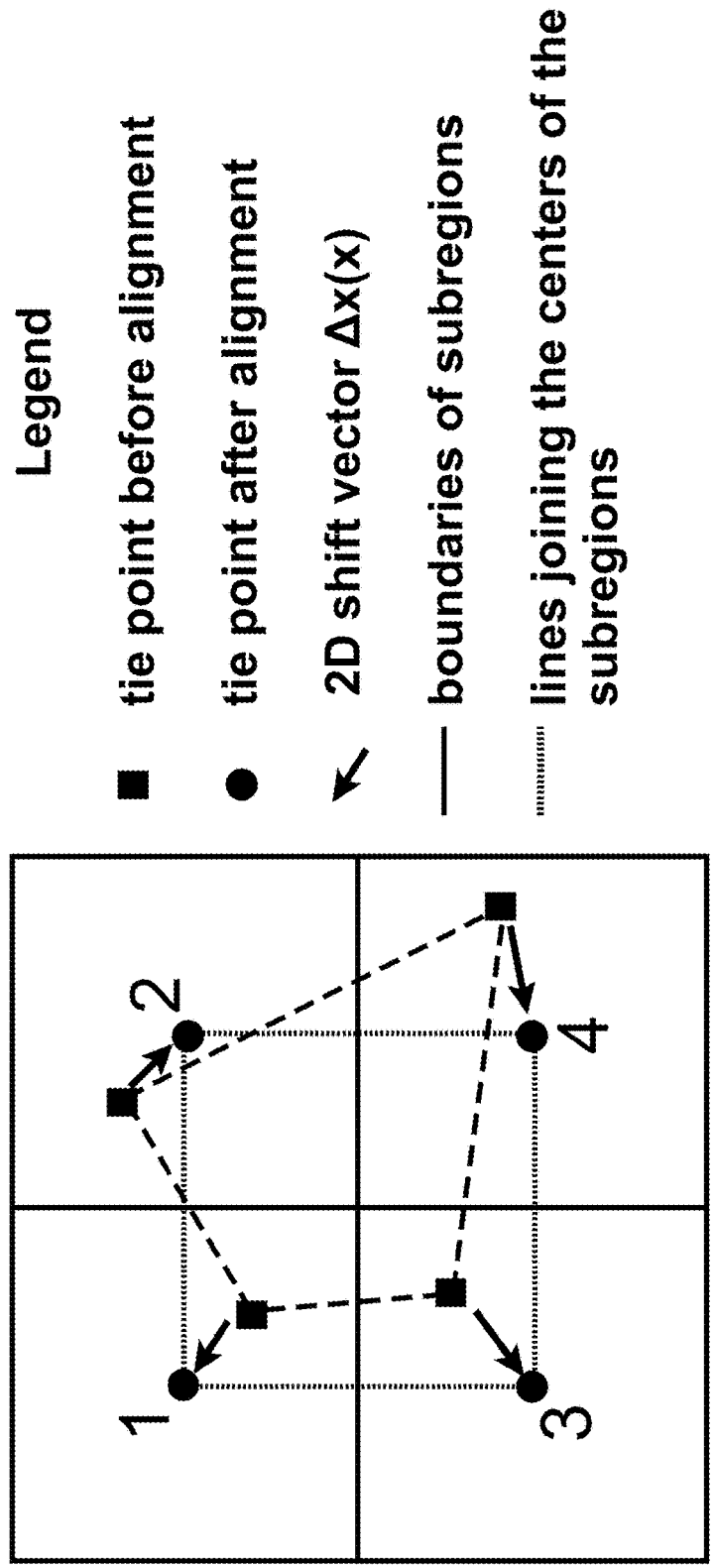
Figure 5: Depiction of the tie points defined for a subregion of the image when the tie points are defined on the center of each subregion.

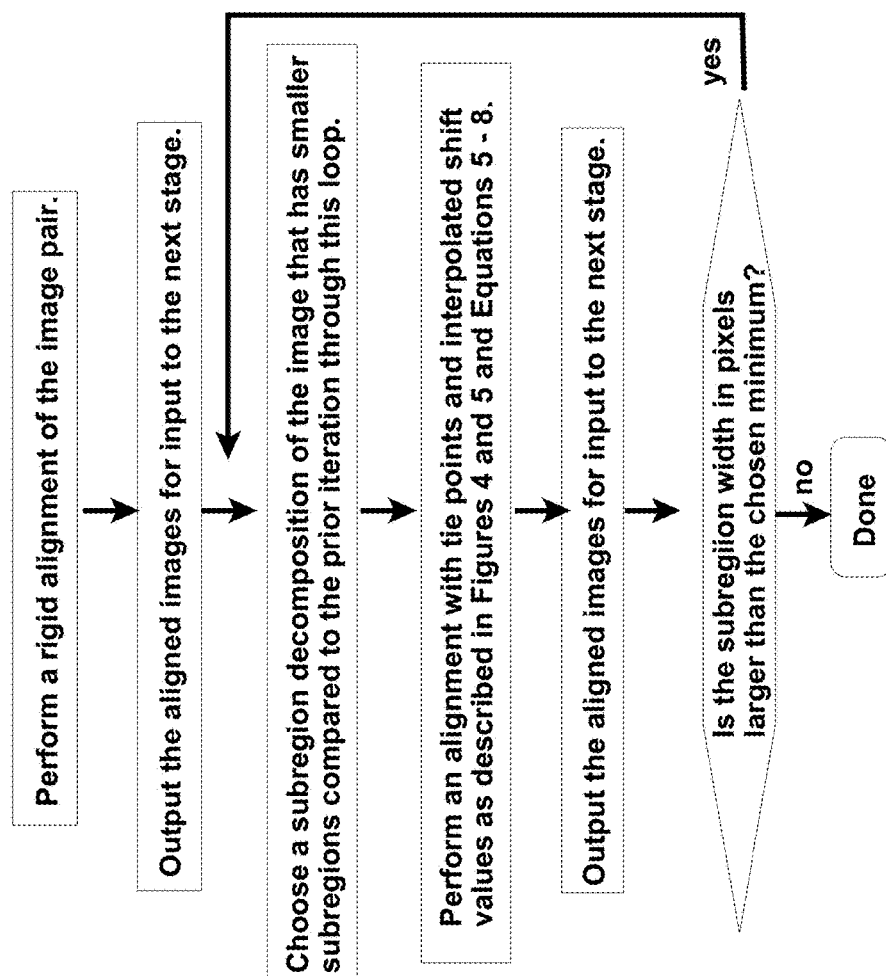
Figure 6: Scheme for recursively decomposing the subregions to facilitate geometric distortion

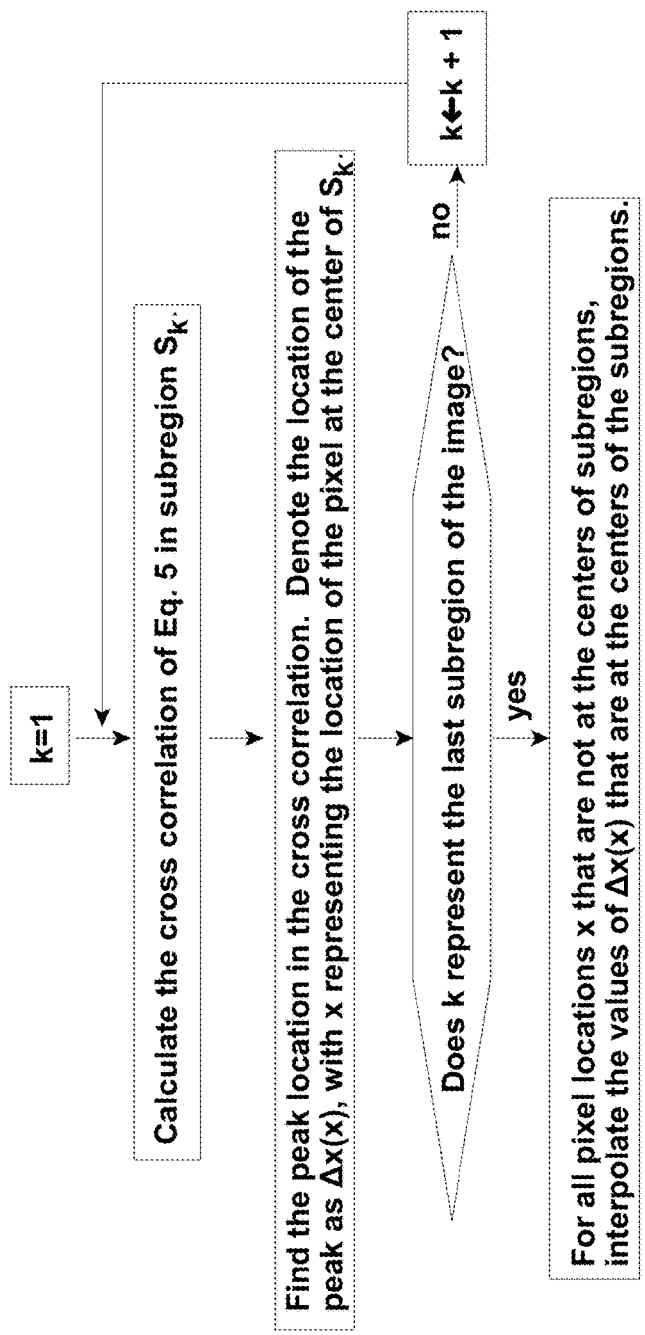
Figure 7: Flowchart of the software program flow that steps through the subregions to facilitiate alignment with geometric distoration correction.

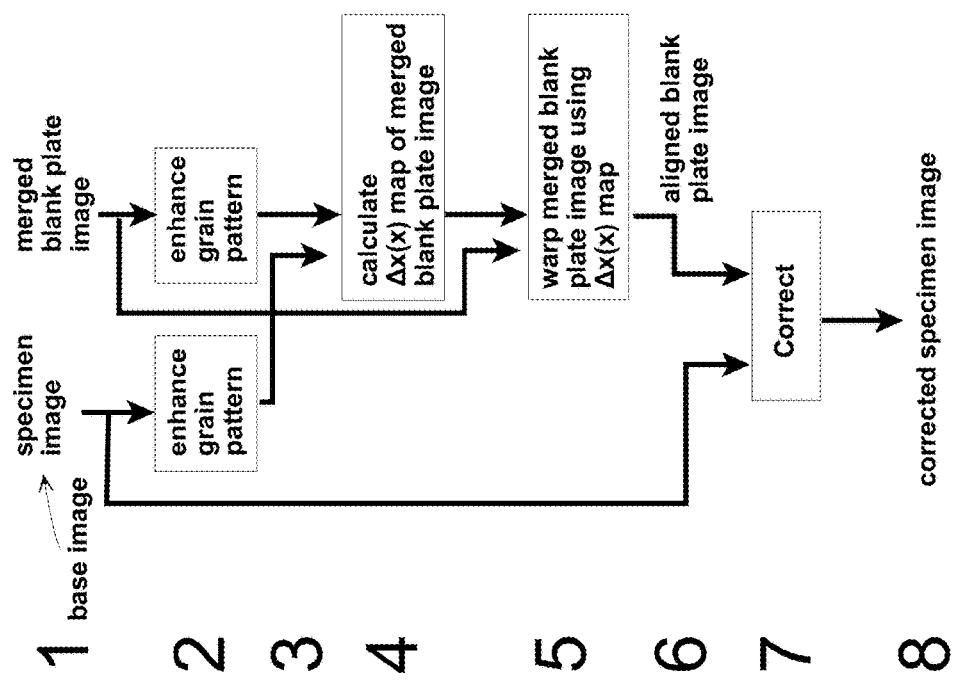
Figure 8: Process flow for correcting the specimen image for sensitivity nonuniformity.

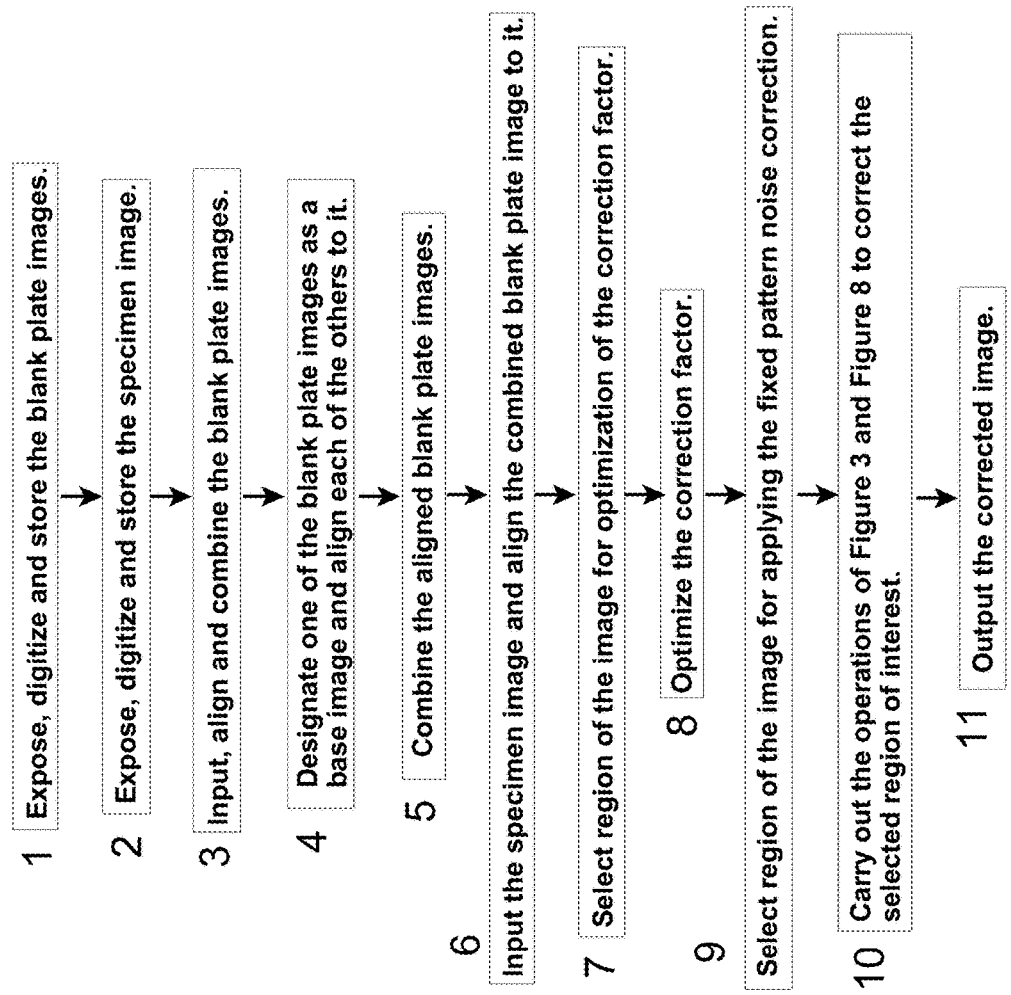
Figure 9: Workflow steps for sensitivity function correction

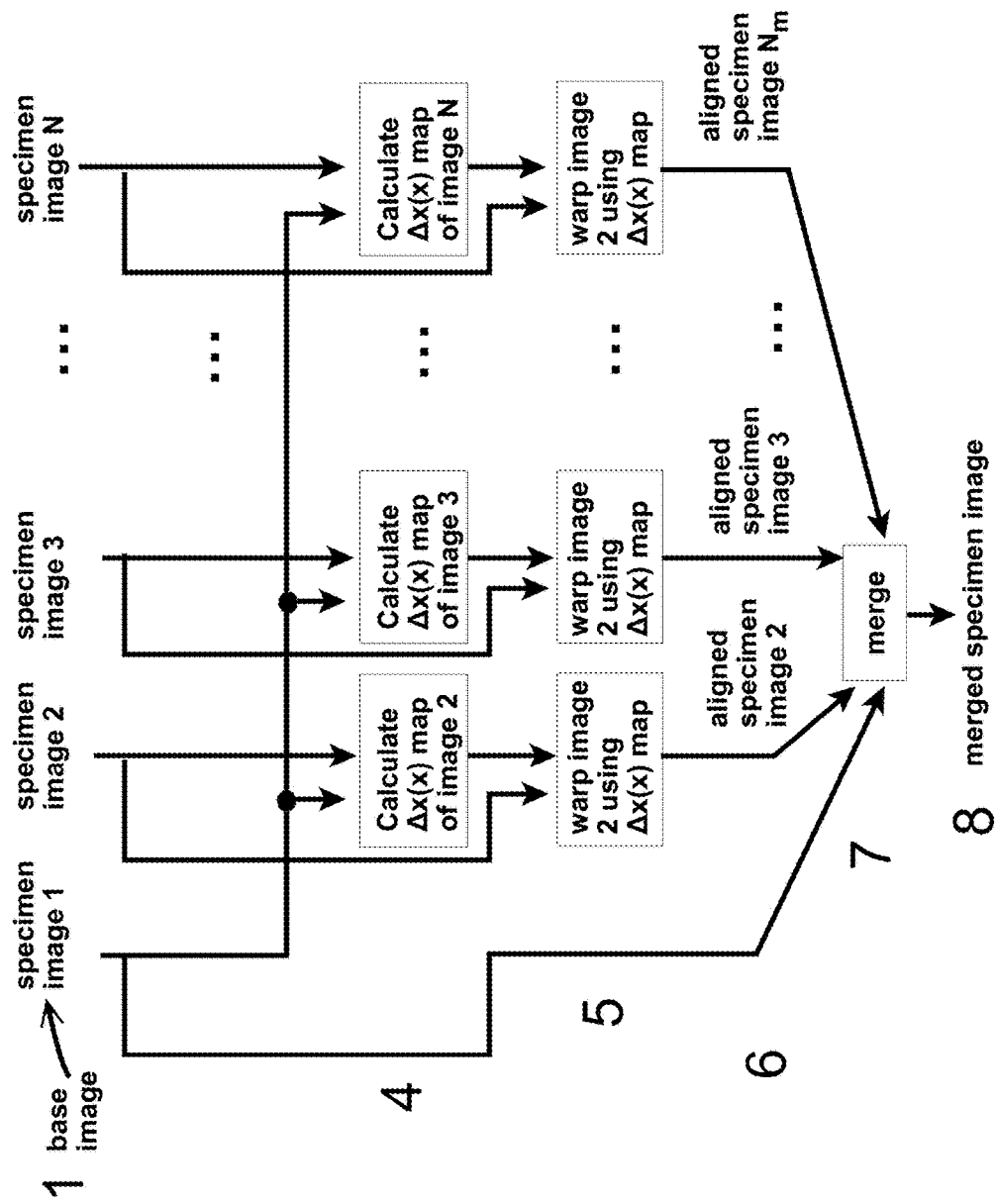
Figure 10: Scheme for aligning and merging specimen images

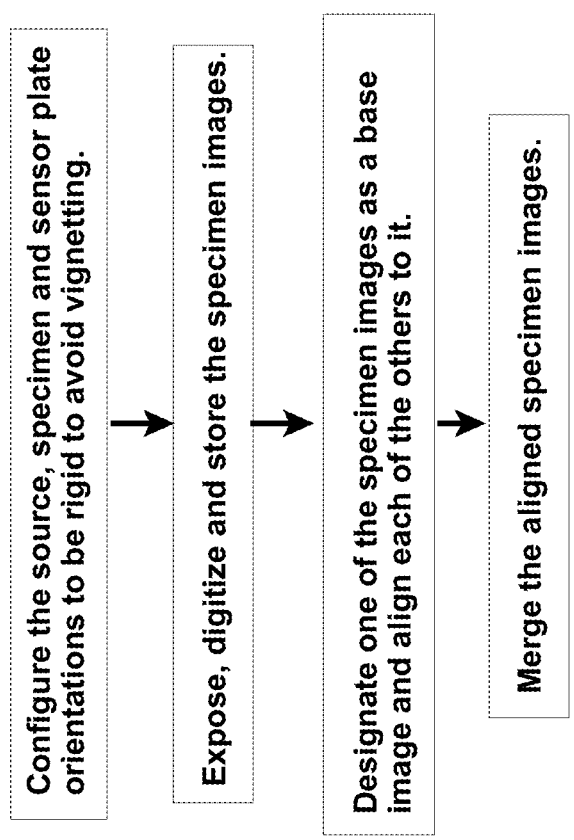
Figure 11: Workflow for exposing and merging specimen images.

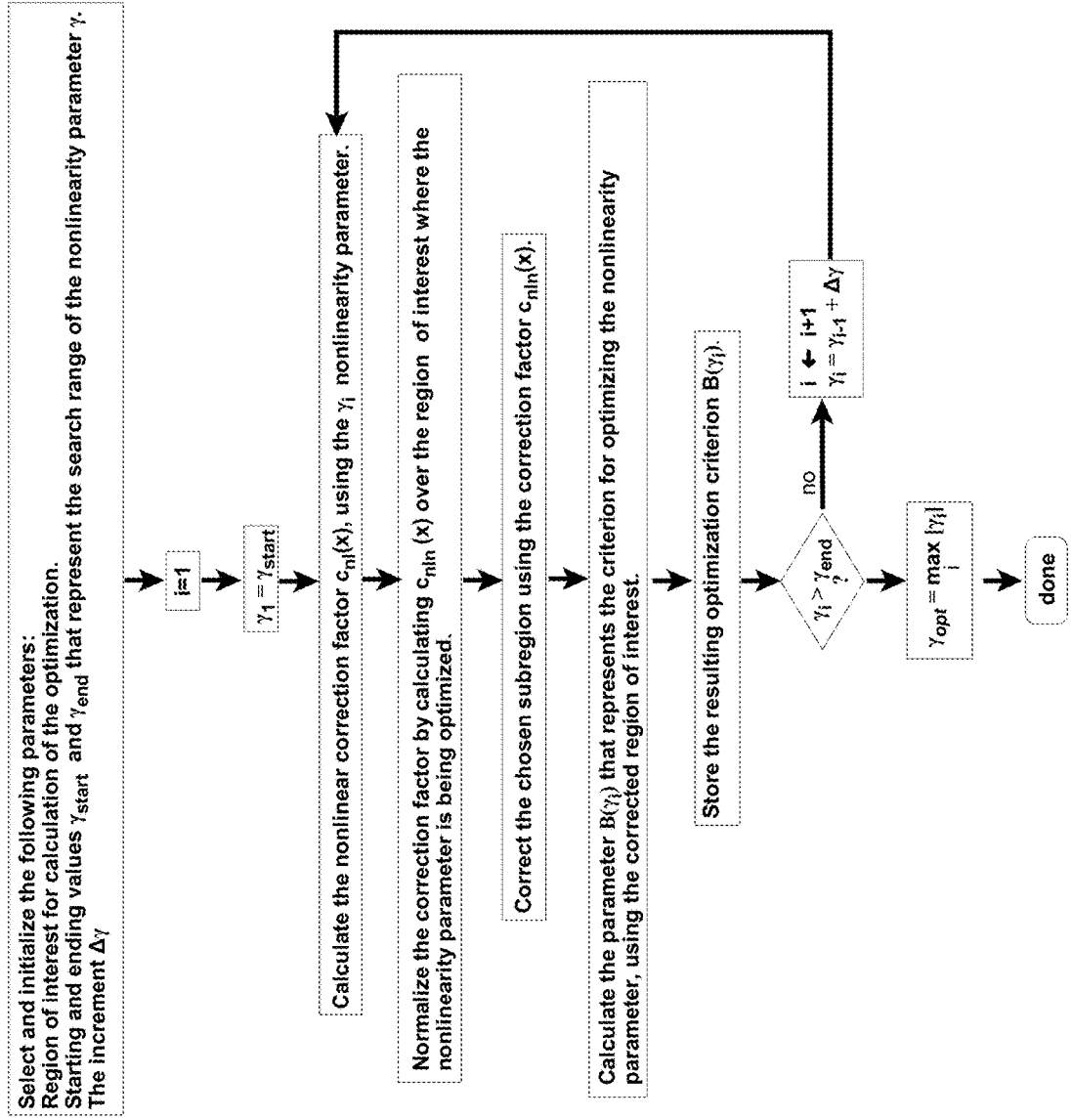
Figure 12: Scheme for optimizing the nonlinearity parameter

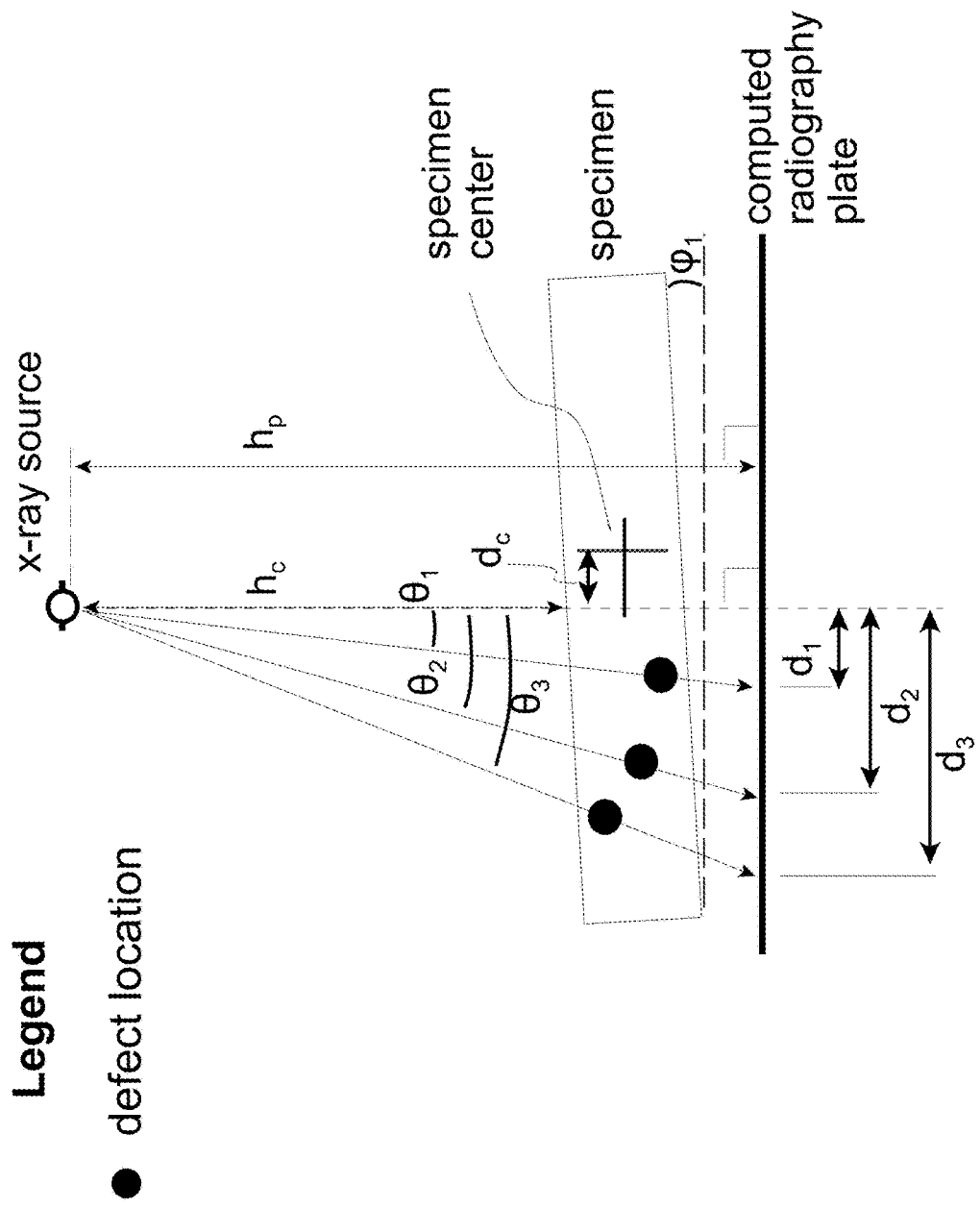
Figure 13: Illustration of errors that can be caused by vignetting

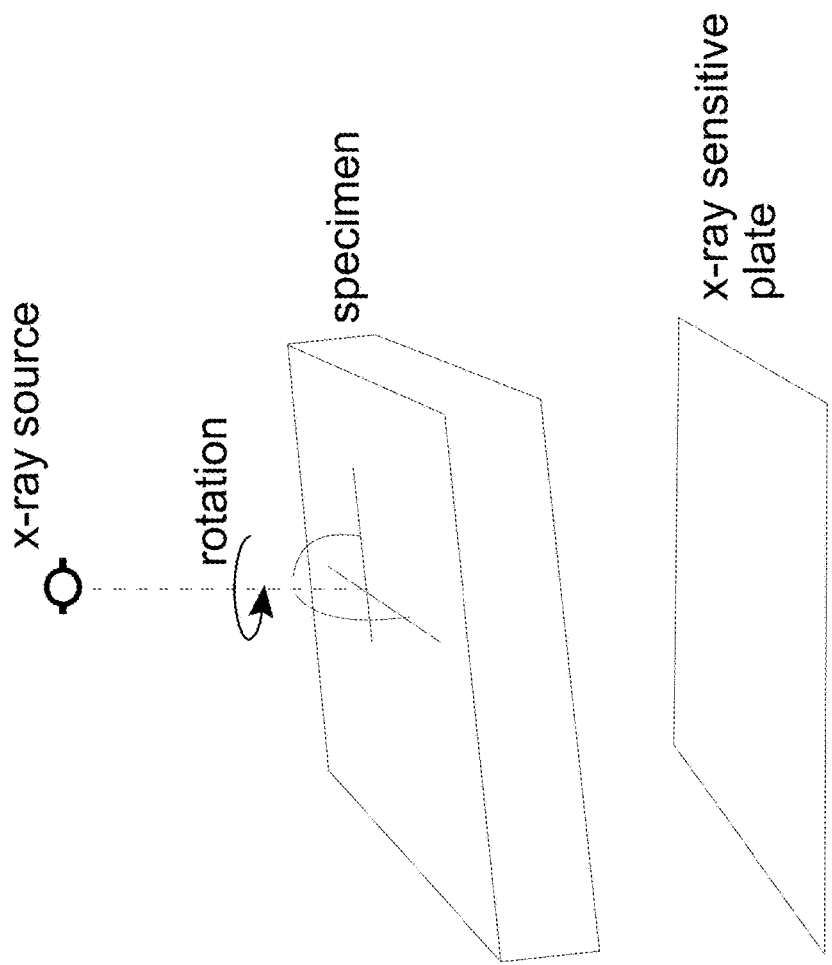
Figure 14: Illustration of 3D aspects of the rigid orientation that is needed between the x-ray source and specimen in order to avoid vignetting

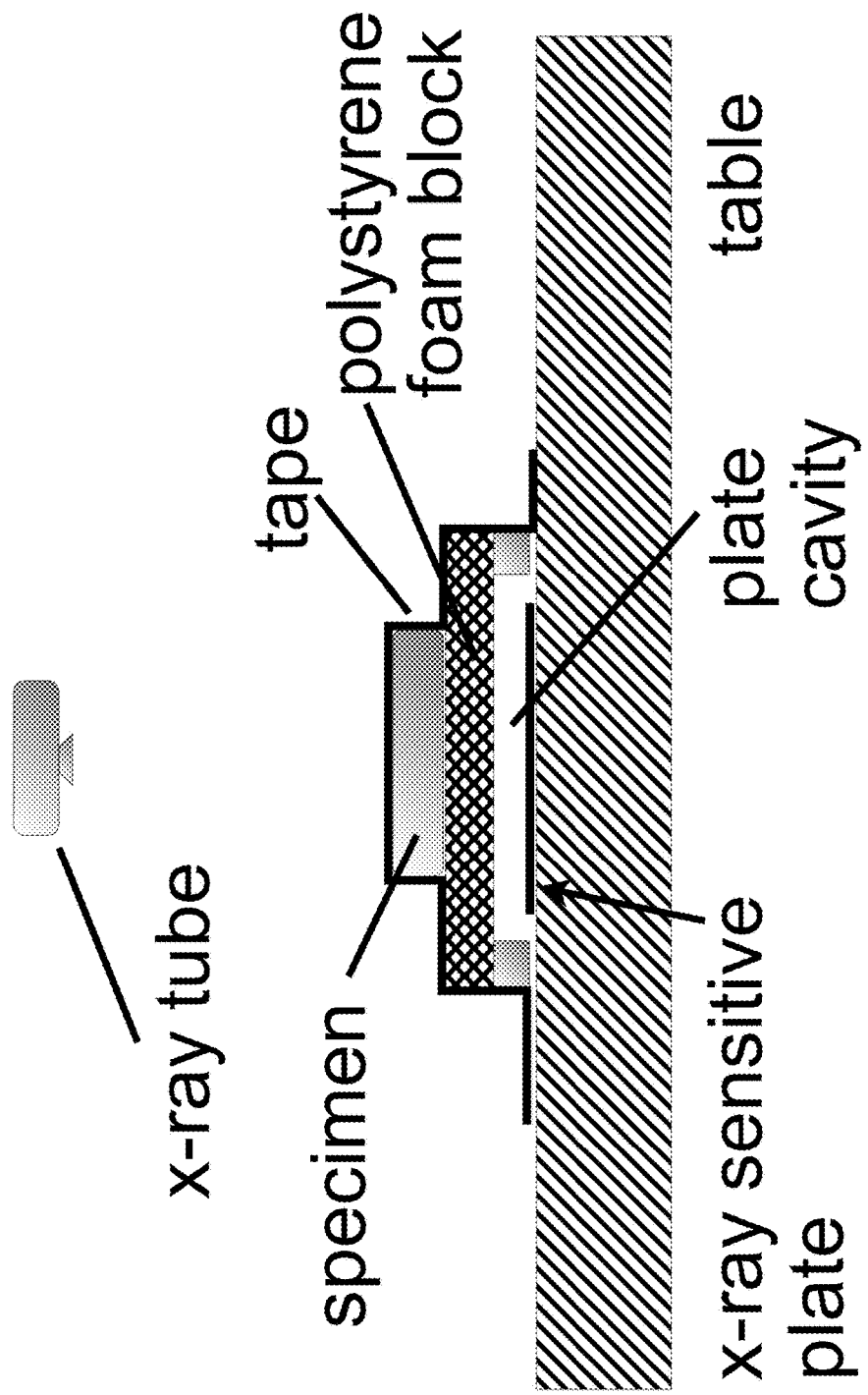
Figure 15: A rigidity device

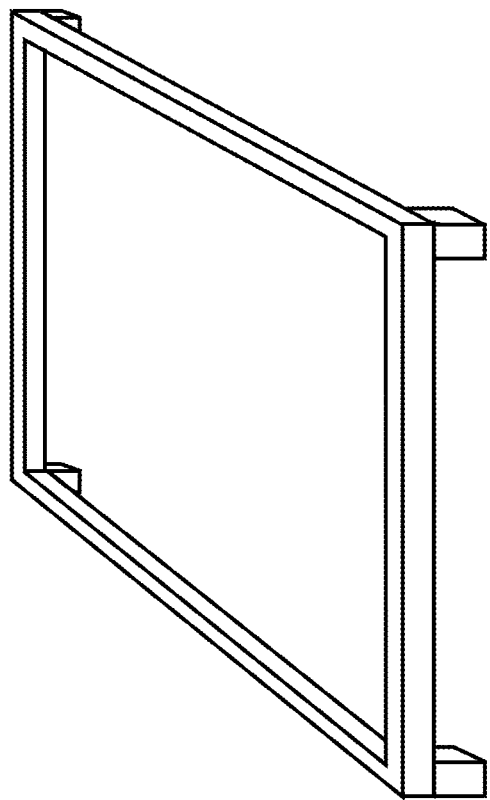
Figure 16: Example of a rigidity device made of dense material

COMPUTED RADIOGRAPHY CONTRAST, NOISE AND RESOLUTION IMPROVEMENT

PRIORITY

This application claims priority to U.S. provisional application 62/523,013, entitled, TECHNIQUES FOR IMPROVED COMPUTER RADIOGRAPHY, filed in Jun. 21, 2017.

TECHNICAL FIELD

The present invention relates generally to computed radiography, and more particularly to a system and method of enhancing radiographic images produced using phosphor image plates.

BACKGROUND

Computed radiography (e.g., as defined under ASTM Standard E2007; and ASTM Standard E2445) is a modality of planar x-ray imaging. The radiograph is recorded on a flexible sensor plate that contains a thin phosphor layer. The image is stored within the thin layer by the energy states of the electrons in the crystal lattice of the phosphor. A plate based on this mechanism is called a photostimulable phosphor plate. The image is converted from this analog format to a digital format using a computed radiographer reader. The reader is a confocal laser scanning device, called a read out unit, that interrogates the phosphor layer by a raster scan by a point-focused laser. The phosphor responds to the laser by emitting light with an intensity proportional to the density of the excited electrons. A photosensitive detector (e.g., photomultiplier) has its sensor aperture focused onto the same point as the laser. The detector senses the magnitude of the resulting fluorescence and electronically passes the intensity to an analog-to-digital converter that outputs the digital reading to a host-computer's peripheral input device. The digitized image is placed into a computer memory such as a standard hard disk or random access memory. The computer formats the scanned series of digital readings into a 2D image format with rows of pixels. Advantages of computed radiography compared to conventional film radiography (e.g., ASTM Standard E94) include an avoidance of the complexities, expense, risks and potential environmental hazards of chemical film processing.

Computed radiography is a different modality than digital radiography (e.g., ASTM Standard E2736). With digital radiography the sensor plate is directly attached to the computer that holds the images. The x-ray intensities are sensed by a pixelated solid-state digital detector, sometimes called a flat-panel sensor, that is electronically attached to the computer system.

SUMMARY OF THE INVENTION

The present invention involves systems and processes that improve the fidelity of computed radiography images. These solutions compensate for physical effects that limit contrast, noise and spatial resolution. The mathematical underpinnings of the solutions are based upon models of the physical effects of computed radiography data collection and digitization. The solution includes: calibration of a spatially dependent sensitivity pattern of the x-ray sensitive sensor plates; automatic alignment of the sensitivity pattern to the radiographic image; and correction of inherent noise that is caused by the grainy phosphor density of the sensor plate. No fiduciary marks are required to align and process images.

Further features include merging repeated image exposures of the same specimen in a way that improves the image fidelity by reducing the effects of quantum noise and other effects. Multiple images are automatically aligned to one another in order to accurately overlay the specimen details. One disclosed technique of merging the images includes frame averaging. A simple device, called a rigidity device, eliminates problems caused by parallax differences that occur when taking multiple exposures of the same specimen. These aspects likewise require no fiduciary marks.

A further feature includes a process for deconvolving the images in order to improve spatial resolving power.

In a first aspect, the invention provides a method of processing a computed radiographic specimen image to generate an enhanced specimen image, comprising: determining a sensitivity function of a computed radiography (CR) plate from at least one blank plate image, wherein the sensitivity function is a measure of noise caused by a phosphor grain pattern in the CR plate; inputting a specimen image captured using the CR plate; generating a blank plate-to-specimen (B2S) alignment map that provides a correspondence between pixel locations in the sensitivity function and the specimen image; applying a sensitivity function correction algorithm to the specimen image based on the B2S alignment map, wherein the sensitivity function correction algorithm is derived from the sensitivity function; and outputting an enhanced specimen image.

A second aspect of the invention provides a computing system for enhancing computed radiographic images, comprising: a system for determining a sensitivity function of a computed radiography (CR) plate from at least one blank plate image, wherein the sensitivity function is a measure of noise caused by a phosphor grain pattern in the CR plate; a system for generating a blank plate-to-specimen (B2S) alignment map that provides a correspondence between pixel locations in the sensitivity function and a specimen image captured with the CR plate; and a system for generating an enhanced specimen image by applying a correction algorithm to the specimen image using the B2S alignment map, wherein the correction algorithm is derived from the sensitivity function.

A third aspect of the invention provides a computer program product stored on a computer readable medium, which when executed by a computing system, enhances computed radiographic images, comprising: program code for determining a sensitivity function of a computed radiography (CR) plate from at least one blank plate image, wherein the sensitivity function is a measure of noise caused by a phosphor grain pattern in the CR plate; program code for generating a blank plate-to-specimen (B2S) alignment map that provides a correspondence between pixel locations in the sensitivity function and a specimen image captured with the CR plate; and program code for generating an enhanced specimen image by applying a correction algorithm to the specimen image using the B2S alignment map, wherein the correction algorithm is derived from the sensitivity function.

A fourth aspect of the invention provides a method of processing a radiographic image, comprising: inputting a set of specimen images of a specimen captured on a CR plate; spatially aligning the specimen images to one another such that details of the specimen are accurately overlaid, wherein a resulting spatial aligned images compensate for spatially varying geometric distortions; and merging the spatially aligned images into an enhanced specimen image having reduced image noise.

A fifth aspect of the invention provides a method of processing a radiographic image, comprising a deconvolution algorithm that improves spatial resolving power.

A sixth aspect of the invention provides a method of processing a computed radiographic specimen image to generate an enhanced specimen image, comprising: inputting a blank plate image captured using a computed radiography (CR) plate; inputting a specimen image using the CR plate; calculating spatial misalignments between the specimen image and the blank plate image by analyzing similarities in phosphor grain patterns between the specimen image and the blank plate image; generating an enhanced image that compensates for a spatially varying sensitivity of the CR plate based on the spatial misalignments; and outputting the enhanced specimen image.

A seventh aspect of the invention provides method of processing a computed radiographic specimen image to generate an enhanced specimen image, comprising: inputting a plurality of blank plate images using a CR plate; calculating first spatial misalignments among the plurality of blank plate images by analyzing similarities in phosphor grain patterns of the blank page images; inputting a specimen image using the CR plate; calculating second spatial misalignments between the specimen image and the blank plate images by analyzing similarities in phosphor grain patterns between the specimen image and the blank plate images; generating an enhanced image that compensates for a spatially varying sensitivity of the CR plate based on the second spatial misalignments; and outputting the enhanced specimen image.

BRIEF DESCRIPTION OF THE DRAWINGS

FIG. 3 depicts a process flow for aligning and merging blank plate images.

FIG. 4 depicts the progressive decomposition of subregions for alignment with geometric distortion.

FIG. 5 depicts the tie points defined for a subregion of the image when the tie points are defined on the center of each subregion.

FIG. 6 depicts a scheme for recursively decomposing the subregions to facilitate geometric distortion.

FIG. 7 depicts a flowchart of the program flow that steps through the subregions to facilitate alignment with geometric distortion correction.

FIG. 8 depicts a process flow for correcting the specimen image for sensitivity nonuniformity.

FIG. 9 depicts workflow steps for sensitivity function correction.

FIG. 10 depicts a scheme for aligning and merging specimen images.

FIG. 11 depicts a workflow for exposing and merging specimen images.

FIG. 12 depicts a scheme for optimizing the nonlinearity parameter.

FIG. 13 depicts an illustration of geometric errors that can be caused by parallax.

FIG. 14 depicts an illustration of 3D aspects of the rigid orientation that is needed between the x-ray source and specimen in order to avoid parallax changes among images.

FIG. 15 depicts a rigidity device.

FIG. 16 depicts a rigidity device made of dense material.

Figure 1:
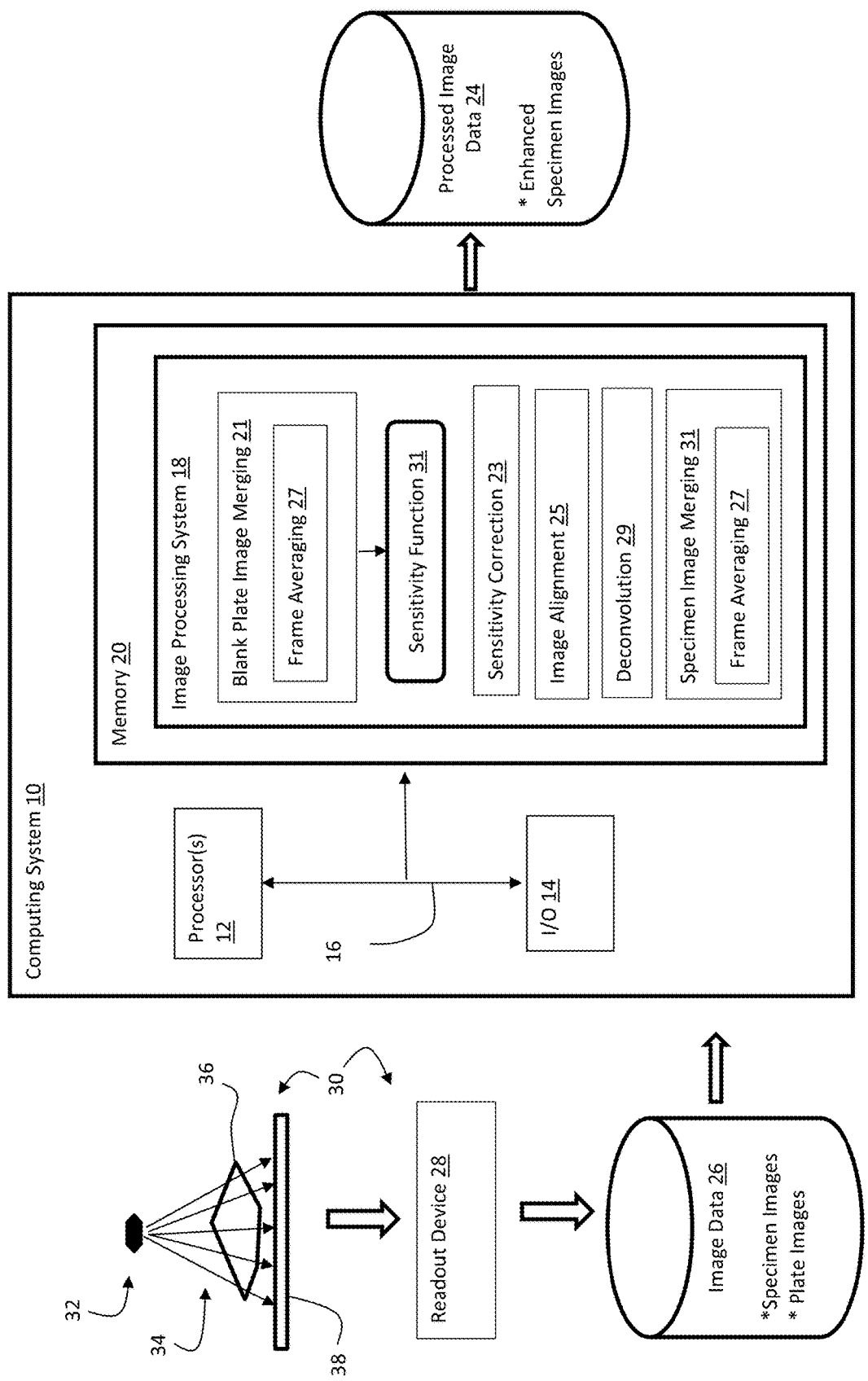
FIG. 1 depicts a system for collecting and processing CR image data.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

System Overview

FIG. 1 depicts a computed radiography (CR) system that generally includes (1) a CR apparatus 30 for collecting image data 26, and (2) an image processing system 18 that processes the image data 26 and generates processed image data 24. CR apparatus 30 generally includes an x-ray source 32 that emits x-rays 34 through a specimen 36 and onto a photostimulable phosphor (PSP) plate 38. A readout device 28 is then utilized to read information from the plate 38, digitize the information, and store pixel based image data 26.

Plate 38 contains an x-ray sensitive phosphor layer that stores the x-ray pattern by excited electron states of its internal molecules. The phosphor has a spatially nonuniform density that is sometimes called the grain density. This grain density has a relatively uniform distribution across the plate 38 when envisioned macroscopically. However, when examined microscopically, the density is randomly nonuniform and grainy in texture. As a result, when small portions of an image is examined at a high digital magnification, the image shows a grainy noise pattern. This noise pattern overlays the details of the specimen that are of interest to the examiner. It contributes to the noise level of the image and degrades image fidelity. Despite the fact that the noise exhibited by the plate 38 is random in appearance, the phosphor grain pattern, and thereby the sensitivity function that it causes, are predictable in that they remain nearly the same from one x-ray exposure to the next, as long as the same computed radiography plate 38 is used.

This predictability characteristic holds within short time frames of minutes, days and weeks or longer. Thereby the sensitivity function caused by the phosphor grain pattern is recordable using the CR apparatus and read out device 28 in FIG. 1. The recorded sensitivity function can be used to mathematically correct the specimen image and thereby reduce its degrading effect on the image fidelity. As shown in FIG. 1, this process is implemented by image processing system with a sensitivity correction module 21.

After correcting the radiograph for these effects, the characteristics of the specimen 36 that are under inspection become more clear because the processed image data 24 is less dominated by noise. Important details such as cracks, voids, inclusion, porosity, density, crystal grain and material boundaries are easier to see and may be more accurately evaluated or measured.

Another aspect of image processing system 18 includes a blank plate image merging module 21 that for example utilizes frame averaging 27 to reduce image noise. A challenge of blank plate image merging involves the relative spatial alignment of the blank plate as it is fed through and processed by the readout device. The plate's grain pattern in relation to the digitized pixels moves from one x-ray exposure to the next. This movement causes the grain pattern on the plate 38, to move, from one digitized blank plate image to the next. Image alignment module 25 is utilized to correct this effect so that coinciding locations of the grain pattern overly each other accurately, by occurring at the same location of the blank plate images, from one exposure to the next.

Another aspect of image processing system 18 includes an alignment of the merged blank plate image with the image of the specimen in order to affect a correction of the grain pattern. A challenge of grain pattern correction involves the relative spatial alignment required among the x-ray source, specimen and computed radiography plate 38. The plate's position in relation to the specimen 36 and source 32 typically moves from one x-ray exposure to the next. This movement causes the grain pattern image, that is inherently overlain with the specimen, on the digitized image, to move. Image alignment module 25 is utilized to correct this effect so that coinciding locations of the grain pattern in the merged blank plate image overly with the grain pattern in the aligned specimen image, by occurring at the same pixel location of the image.

Another aspect of image processing system 18 includes merging of specimen images by specimen image merging module 31. A challenge of specimen image merging with computed radiography involves the relative spatial alignment required among the x-ray source, specimen and computed radiography plate 38. The plate's position in relation to the specimen 36 and source 32 typically moves from one x-ray exposure to the next. This movement causes the specimen image on the plate 38, to move. Image alignment module 25 is utilized to correct this effect so that coinciding locations of the specimen 36 overly each other accurately, by occurring at the same location of the image, from one exposure to the next.

In one illustrative embodiment, a sensitivity correction module 23 is applied to the specimen images and an image merging module 21 is applied to the resulting corrected images to compound their noise reduction benefits.

In a further aspect, a spatial deconvolution module 29 may be implemented to improve the resolving power of a radiograph (i.e., image data 26) to compensate for inherent resolution limits and produce an output image that has a resolving power improved compared to the input image. The predominant causes of resolving power limits are listed in Table 1.

TABLE 1

Causes of resolving power limits

| | | |
|---|---|---|
| 1. | source spot size | The x-ray energy emanates from the source from a spot on the x-ray sources target that has a finite size. |
| 2. | Compton scatter | Compton scatter [Macovski] deflects the x-ray beam in both the specimen and the plate. |
| 3. | light scatter | The fluorescent light, that emanates from the plate in the read out unit, diffuses among the plate's materials before exiting, causing a blurring of the exiting light energy. |
| 4. | confocal optics | The laser scanning and light detection system of the read out unit is a confocal microscope, which has a diffraction-limited spatial resolution [Pawley] |
| 5. | dwell time | Each pixel reading that is digitized by the analog-to-digital converter of the read out unit is affected by an integration time, wherein the light intensity is effectively integrated over a short time frame. The laser spot and point detector focus are spatially moving during this dwell time, which causes a spatial blur in the direction of the scan. |
| 6. | pixel size | Each image pixel represents a spatially integrated light intensity emanating from the plate. A typical pixel size is 50 micrometers, although smaller and larger sizes are also typical. |

To an approximation, the specimen radiograph follows a model according to:

$$g(x)=f(x)*h(x), \quad (1)$$

where the mathematical terms are defined in Table 2. Noise is ignored in this expression and is considered later in this document.

TABLE 2

Mathematical terms

| | | | |
|---|---|---|---|
| x | 2D spatial coordinate of the image. | f(x) | ideal specimen image with no degradation due to noise or resolving power |
| h(x) | point spread function that characterizes the resolving power [Pawley; Macovski] | | |
| g(x) | digitized image under ideal conditions where the resolution limit is considered but the sensor plate's sensitivity function and other noise sources are ignored | Δx(x) | Alignment map - A map of the 2D shift that is applied to the input image at 2D location x of the output image in order to align the image to a base image. |
| $N_b$ | Number of blank plate images | s(x) | Sensitivity function that characterizes the phosphor grain pattern |
| $g_s(x)$ | Digitized Image of the specimen with the sensitivity function considered and with other noise sources described in Items 1, 3, 4, 5 and 6 of Table 3 ignored. | n(x) | noise of the type described in Items 1, 3, 4 and 5 of Table 3. |
| $g_n(x)$ | Digitized image of the specimen with the sensitivity function and other noise sources considered. | $\hat{g}(x)$ | Estimate of g(x) produced by applying a correction technique to the digitized image $g_n(x)$ |
| ★ | Cross correlation operator | $g_1(x)$ | Base image in the cross correlation operation. |
| $g_2(x)$ | Image that is being aligned to $g_1(x)$ when considering the cross correlation operator | R(x) | cross correlation function |
| $R_{rot}(r,\theta)$ | cross correlation function, where the input function that is designated as the one being shifted is first rotated by angle θ | $g_{2\_rot}(x,\theta)$ | $g_2(x)$ rotated by angle θ. |

TABLE 2-continued

Mathematical terms

| | | | |
|---|---|---|---|
| $\Delta x_{h,i}$ | horizontal component of the alignment shift vector at subregion center i (FIG. 5) | $\Delta x_{v,i}$ | vertical component of the alignment shift vector at subregion center i (FIG. 5) |
| $x_{h,i}$ | horizontal coordinate of the center of subregion i. | $x_{v,i}$ | vertical coordinate of the center of subregion i. |
| $c_{h,j}$ | j-th coefficient of the polynomial expression for the horizontal component of the alignment shift | $c_{v,j}$ | j-th coefficient of the polynomial expression for the vertical component of the alignment shift |
| $S_k$ | k-th subregion of pixels used during the alignment process | $c(x)$ | correction factor |
| $\varepsilon$ | empirical constant for Wiener-type regularization | $c_{nl}(x)$ | nonlinear correction factor |
| $\gamma$ | nonlinearity parameter | $\gamma_{opt}$ | optimal nonlinearity parameter |
| $\gamma_i$ | the i-th value of $\gamma$ that is being tested while searching for $\gamma_{opt}$ | $\gamma_{start}$ | the starting value of the range of values of $\gamma$ that will be tested |
| $\gamma_{end}$ | the ending value of the range of values of $\gamma$ that will be tested | $\Delta\gamma$ | the increment between values of $\gamma_i$ |
| $\gamma_{opt}$ | optimal nonlinearity parameter | | |
| $a_i$ | coefficients that together make a set of nonlinearity parameters | $c_{nln}(x)$ | normalized nonlinear correction factor |
| $S_{roi}$ | Set of pixels, or x locations, that make up the region of interest | $B(\gamma)$ | Objective function that is minimized as the criterion for selecting the optimal nonlinearity parameter $\gamma$. |
| $x_h$ | horizontal component of x | $x_v$ | vertical component of x |
| $\Delta x_h$ | spatial distance (e.g., in meters) between the centers of two adjacent pixels in the horizontal direction | $\Delta x_v$ | spatial distance (e.g., in meters) between the centers of two adjacent pixels in the vertical direction |
| $m_{roi}$ | Mean image value in the pixels in the region of interest $S_{roi}$ | L | I divergence function |
| $\hat{g}_s(x)$ | estimate of $g_s(x)$ | | |
| $\hat{f}(x)$ | estimate of $f(x)$ | $\hat{h}(x)$ | estimate of $h(x)$ |
| $\alpha_f$ | overrelaxation parameter for the iterative estimate of $f(x)$ | $\alpha_h$ | overrelaxation parameter for the iterative estimate of $h(x)$ |
| $g_m(x)$ | output image resulting from the merger of images | $g_{al,i}(x)$ | aligned specimen image i |
| $N_m$ | number of merged images | $\Delta\hat{f}(x)$ | iterative change applied to $\hat{f}(x)$ in the deconvolution algorithm |
| $\Delta\hat{h}(x)$ | iterative change applied to $\hat{h}(x)$ in the deconvolution algorithm | $h_c$ | distance from the x-ray source to the specimen |
| $h_p$ | distance from the x-ray source to the sensor plate | $\varphi_1$ | angle of orientation between the specimen and a plane parallel to the sensor plate |
| $\theta_1, \theta_2, \theta_3$ | angle of projection line from the x-ray source to the sensor plate through specific defect points | $d_1, d_2, d_3$ | distance from the specimen center to the projection of the defect center on the sensor plate |
| $d_c$ | distance from the vertical line to the specimen center, where the vertical line traverses through the x-ray source and forms a right angle with the sensor plate | k | index for counting the loop number that is being executed and that is defining the subregion number in FIG. 7 |
| $w_g(x)$ | weighting function for the iterative correction objective function that estimates $g(x)$ | | |
| $w_f(x)$ | weighting function for the deconvolution objective function gradient term for $\hat{f}(x)$ | $w_h(x)$ | weighting function for the deconvolution objective function gradient term for $\hat{h}(x)$ |

A point spread function, which is also called the impulse response, characterizes the resolution limit. More particularly, one or more parameters of the point-spread function may characterize the resolution limits. In optical imaging systems and medical imaging systems, the full-width-at-half-maximum is one such parameter that is often used. In x-ray radiographic systems, including film, digital and computed radiography, the basic resolution and image unsharpness are two such parameters [ASTM Standard E2002].

By using known deconvolution algorithms in this context, resolving power can be improved by a factor of 1.5 to 3.0. Improvement by a factor of 1.5 to 2.0 is generally easy to obtain while improvement factors around 3 are more difficult to achieve. Attempts to tune a deconvolution algorithm to produce higher improvements in resolution may amplify noise and edge artifacts, so there is a tradeoff between resolution and noise. However, there is no known theoretical limit to the resolution improvement, so the invention is not intended to be limited as such. The deconvolution module 29 may be used coincidentally with the sensitivity correction module 21, image merging module 23 or both to compound the improvements in image fidelity.

Process Overview

Figure 2:
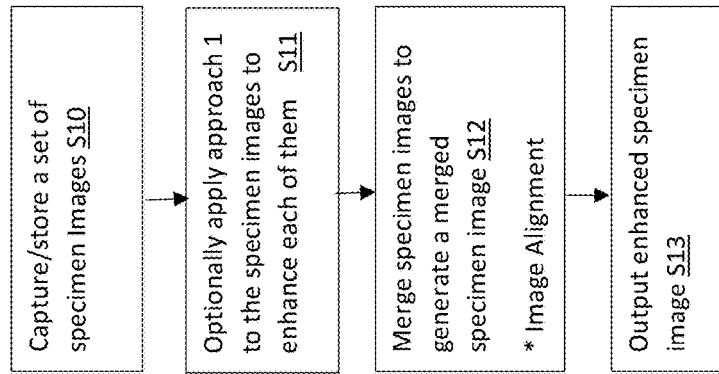
FIG. 2 depicts flow diagrams showing two approaches for generating enhanced CR images.
Figure 2:
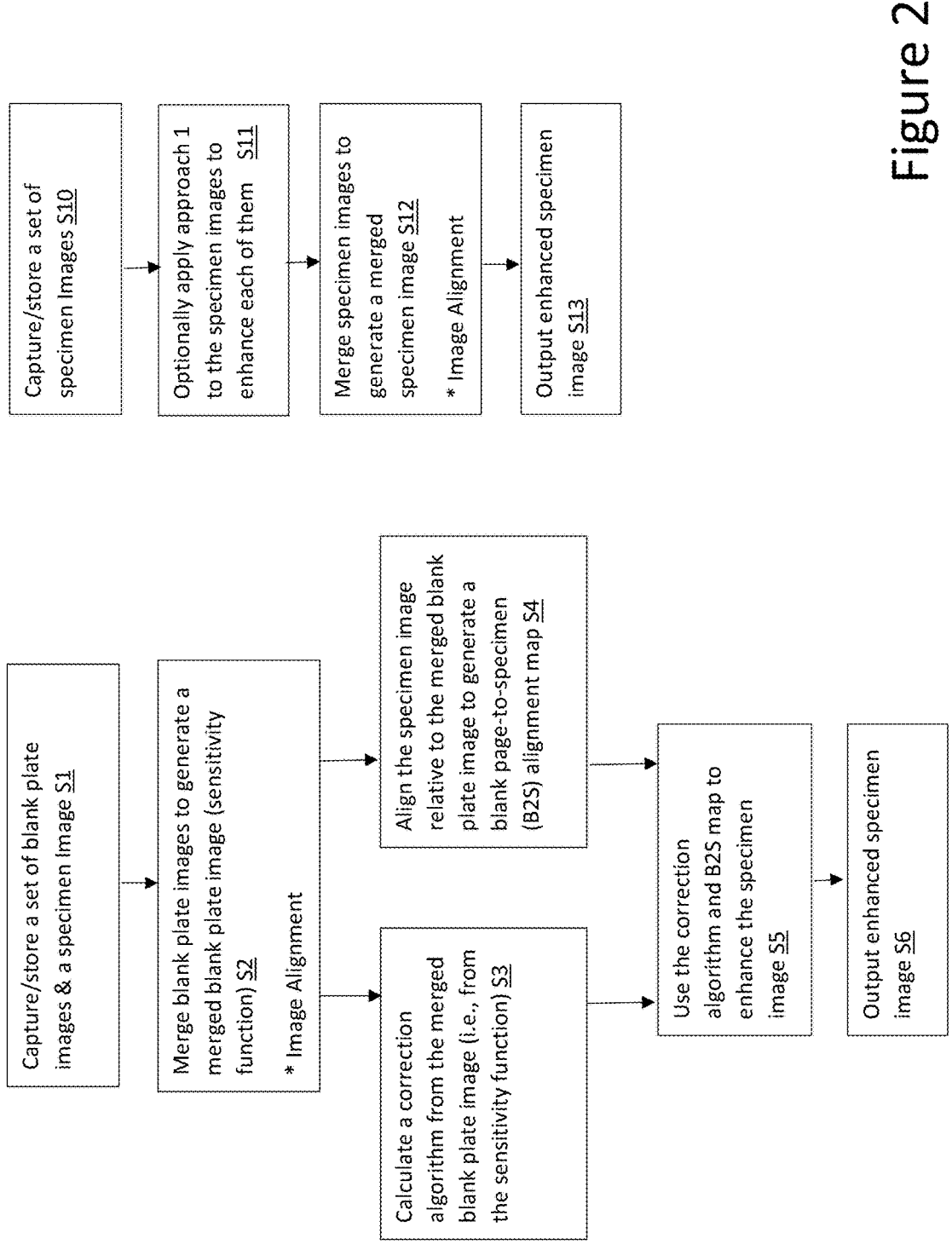

FIG. 2 depicts a pair of flow diagrams showing high level overviews of two enhancement approaches using the system of FIG. 1. Approach 1 (left hand diagram) analyzes a set (i.e., one or more) of captured images of a blank plate to enhance a specimen image while approach 2 analyzes a set of captured images of the specimen to generate an enhanced specimen image. Neither process requires the use of fiduciary marks to align images.

Beginning with approach 1, a set of blank plate images are captured and stored along with a specimen image at S1. At S2, the blank plate images are merged (using image alignment) to generate a merged blank plate image which provides a sensitivity function. At S3, a correction factor is calculated based on the sensitivity function. At S4, the merged blank plate image (i.e., sensitivity function) is aligned relative to the specimen image to created a blank plate-to-specimen (B2S) alignment map. FIG. 8 and most of the discussions illustrate this B2S alignment map by a description where the blank plate image pixels move and the specimen image pixels do not move. However, the B2S alignment map may be calculated and used antipodally, where the specimen image pixels move, the blank plate image pixels do not move, and the B2S alignment map specifies the movement of the specimen image pixels. The B2S process and map as provided herein are intended to include both of these antipodal operations. At S5, the correction algorithm and B2S alignment map are utilized apply a sensitivity correction to the specimen image, and at S6, an enhanced specimen image is output.

In approach 2, a set of specimen images are captured and stored at S10, and at S11 the specimen images are optionally merged (using image alignment) to generate a merged specimen image at S12. At S13, the enhanced specimen image is output.

Sensitivity Correction

In the present context, the term noise refers to random fluctuations in a given pixel value that degrades the image fidelity. In certain contexts, the pixel value may also be called the gray level, image intensity level or other nomenclature. The predominant causes of noise are summarized in Table 3.

TABLE 3

| | | Predominant causes of noise |
|---|---|---|
| 1. | quantum x-ray photon interactions with phosphor | The event of an x-ray photon interacting with an electron in the phosphor is a random occurrence. The number of such events at any given material volume in the phosphor layer is a Poisson distributed random number. |
| 2. | phosphor grain | The density of the phosphor molecules has a spatially random distribution at the microscopic level. This pattern is considered in this approach using a sensitivity function s(x), which is explained in Table 2 and in the Characteristics of the Computed Radiography Plate section. |
| 3. | quantum fluorescent emission | For any x-ray photon interaction, the number of light photons emitted from any material volume in the phosphor layer is a Poisson distributed random number. |
| 4. | photodector quantum noise | For any light photon interaction with the photodector, the number of electrons that produce a current output from the device is a Poisson distributed random number. |
| 5. | electronic noise | The photodetector output signal is input to electronic stages that amplify or attenuate the signal to make it compatible with the voltage or current range of the analog-to-digital converter. These electronic stages produce thermal electrical noise. |
| 6. | Microscopic foreign particles | Examples are dust, lint, hair and air-borne particles that settle onto the computed radiography plate or cassette case. A particle will appear at a location in one image frame and will be gone in another frame since it is not adherent to the plate and can fall away from the plate. |

In the described embodiments, the sensitivity correction module 21 may be utilized to correct the type of noise described in item 2 involving phosphor grains, and the image merging module 23 may be utilized to correct the types of noise described in items 1, 3, 4, 5 and 6 of Table 3.

The type of noise described in item 6 of Table 3 is caused from contaminants that settle on the computed radiography plate or onto the cassette that holds the plate. For example, manufacturing and service environments have dust, lint and other materials floating in the air. Generally, the dust or other material moves about randomly from one radiograph to the next. The dust will blow off of the plate after the exposure and new dust will settle onto a new location. Blemishes, such as scratches, may change on the plate as well.

Blank Plate Images

As noted, every computed radiography plate 38 has a spatially nonuniform x-ray sensitivity pattern. This nonuniformity is caused by its random phosphor grain density, which defines the spatial pattern of it's x-ray sensitivity (i.e., item 2 in Table 3). In the illustrative embodiments, the nonuniformities are measured and corrected. In the first approach described on the lefthand side of FIG. 2, an image of the sensitivity pattern is collected by exposing a blank plate to x-rays, i.e., without a specimen 36 to generate a blank plate image.

Other aspects of the physics, instrumentation and configuration of CR apparatus 30 cause nonuniformities that degrade the image fidelity. The x-rays that emanate from the x-ray source 32 have an angular density that is nonuniform with respect to the angular orientation of their exit from the source 32. This nonuniformity causes shading in the captured image. The blank plate image captures some of these shading effects that then are inherently incorporated into the correction factor image explained in further detail below.

The quantum character of x-ray photons is one of the causes of noise [ASTM Standard E2007]. A random number of x-ray photons interact with the phosphor molecules, so the pixel value that is later produced from these activated molecules is also random. This randomness causes noise in the blank plate images that are used to measure the sensitivity function. The measurement of the sensitivity function is more effective if the quantum noise and other noise sources (items 3-6 in Table 3) are reduced in the process. Merging blank plate images as detailed herein below in FIG. 3 achieves this reduction. Frame averaging module 27 provides one illustrative technique to merge the images. Doing so will produce an averaged blank plate image whose spatial noise pattern is mostly due to the phosphor grain. When frame averaging 27 is applied, the average at each pixel location is calculated. This average is calculated over all the blank plate images. Calculating the median at each pixel location, with the median calculated over the $N_D$ different images, is also effective. Another choice is the square root of the sum of the squares. Other choices of merging the images are also possible, such as an averaging, median or other operation that is modified by removing outliers in the samples, or modified by rank-ordering the values and including only an inner percentage of the values in the averaging or median calculation.

Before merging, the blank plate images must be spatially aligned to one another so that their sensitivity functions, which represent their phosphor grain patterns, are overlain accurately. Embodiments of this alignment operation are described with reference to FIGS. 3-7.

To a rough approximation the degrading effects of the phosphor grain pattern and the many sources of noise may be expressed according to:

$$g_s(x) = s(x)g(x), \qquad (2)$$

with notation defined in Table 2. The noise described in Items 1, 3, 4, 5 and 6 of Table 3 is ignored in this expression. The noise described in Item 2 of Table 3 is considered because it is inherent in the s(x) function. With the additional types of noise considered (i.e., 1, 3, 4, 5 and 6 of Table 3) considered, the expression becomes:

A naive approach to recovering g(x) by removing the effects of s(x) is to perform the following calculation:

$$\hat{g}(x) = \frac{g_n(x)}{s(x)}. \quad (4)$$

However, this may not be a practical approach because the noise n(x) becomes enhanced when s(x) has small values. More practical approaches that avoid this and other problems are detailed below in the Correction Algorithm section.

Alignment Method

Spatial alignment of the images to one another is thus a component operation in several aspects of the described embodiments. In one aspect, blank plate images are aligned to one another before they are merged (i.e., as detailed in FIGS. 3-7). The phosphor grain pattern in a resulting merged blank plate image is then aligned to the phosphor grain pattern in the specimen image, so that their inherent sensitivity functions are aligned, before applying the correction for the sensitivity function (FIGS. 4-9). With image merging, the specimen details, including the edges of objects, material boundaries and material texture, are aligned to one another (FIGS. 4-7, 10, 11).

Each blank plate image represents an x-ray exposure of the same plate without the specimen present. The image merging reduces the effects of quantum noise and other noise sources (Table 3, Items 3-6). The purpose of doing so with blank plate images is to produce an image that has these noise effects removed and thereby represents only the sensitivity function caused by the phosphor grain pattern. This sensitivity function can then be an input to the algorithm that corrects the specimen image.

The alignment of blank plate images is needed, in part, because of a rigid misalignment of the phosphor grain pattern between the digitized images. Each image is intended to represent the same phosphor grain pattern, but the pattern slightly shifts and rotates between x-ray exposures. This is because the computed radiography plate 38 is never fed into the readout device 28 with the same exact location from one reading to the next. The alignment is needed, as well, because of a geometric distortion that happens between any two images. Geometric distortion may be described as a warp, as described herein with reference to Stage 5 of FIG. 3. There are many causes of the rigid misalignment and geometric distortion between blank plate images. A list of some of the predominant causes is in Table 4. Even though the aspects of feed speed, roller grip and scan speed are well-controlled, an inaccuracy or slippage of just a few microns will require an alignment.

TABLE 4

Some of the causes of geometric distortion between blank plate images

The mechanical feed of the plate into the read out unit has minuscule nonuniformity in speed between readings and within the same reading.
Slippage of rollers that grip and feed the plastic coating of the plate.
The laser scanning speed may vary between readings and within the same reading.
The optical scanner of the laser may exhibit nonlinearity and imperfection in its scan speed.

A similar alignment algorithm is needed for aligning the merged blank plate image to the specimen image. FIGS. 5-9 represent embodiments for this alignment process. Note that while the described embodiment utilizes more than one blank plate image, it is possible to use just one blank plate image and forego the blank plate image merging process, but the results may not be as effective.

After aligning the blank plate images to one another and after aligning the merged blank plate image to the specimen image, their phosphor grain patterns, and thereby their sensitivity functions, are overlain accurately. Before merging, the phosphor grain pattern of each image is first enhanced. By enhancing the phosphor grain pattern, other aspects of the images do not appreciably affect the alignment. Such aspects would create spatial errors in the overlay. For example, the blank plate images may have shading features due to randomness of the x-ray nonuniformity which would otherwise cause errors. Particles, including dust and lint, may settle and move on the plate and cause errors as well. When aligning the blank plate image to the specimen image, the specimen image will have features of the specimen. The enhancement of the phosphor grain pattern causes the alignment algorithm to be affected predominantly by the phosphor grain pattern and to ignore these specimen features. There are many ways to enhance the phosphor grain features. Some prominent algorithms include the unsharp mask and Laplacian of Gaussians. By doing so, the necessity of fiduciary marks is eliminated.

When using image merging, such as frame-averaging, the coincident details of the specimen must be aligned among the independent images, as shown in FIG. 10. In this case the enhancement of the phosphor grain pattern is not used.

Geometric distortion can vary continually over the x locations of the image. Therefore the alignment algorithm must adapt continually over these locations. An algorithm that detects the misalignment at locations that form a grid, like those illustrated in FIGS. 4-7, is effective.

Approach 1 Merger and Alignment of Blank Plate Images to One Another

FIG. 3 depicts an embodiment of the process of merging blank plate images that includes blank plate alignment. The process is shown as eight stages. At Stage 1, a set of blank plate images are collected and inputted. Stage 2 enhances the phosphor grain pattern in the blank plate images to generate a set of enhanced grain images (Stage 3). The enhanced grain images are then utilized to calculate an blank page-to-blank page (B2B) alignment map Δx(x) for each blank page image in Stage 4 in which x refers to pixel locations.

In the embodiment shown here, one of the inputted blank plate images serves as the base image. The B2B alignment map Δx(x) of each blank plate image defines its geometric distortion with respect to the base image. At Stage 5 the blank plate images, except for the base image, are geometrically transformed (i.e., warped) to generate a set of aligned blank plate images (Stage 6). At each pixel location x the term Δx(x) indicates the spatial distance along the vertical and horizontal directions to move the pixel value in order for it to align with its counterpart location in the base image. The operation of merging the aligned blank plate images (Stage 7) to generate a final merged blank plate image (Stage 8) may be accomplished, as mentioned earlier, by summing, averaging, calculating the median, calculating the square-root of the sum of the squares or variations of any of these operations, as well as many others.

Other embodiments of aligning blank plate images may likewise be utilized. For example, blank plate images may be separated into pairs, wherein the images of each pair is aligned to one another first, followed by aligning the pairs to one another. In another embodiment, one image may serve as a base image and thereby the next image aligned to it. This operation may be followed by the resulting aligned output image serving as the base image for the next image in the series, or for a set of remaining images, which may be aligned to this new base image. There are many other combinations of base images and alignment sequences that are effective. The terms B2S and B2S map generally refers to any of these embodiments.

As later shown, the outcome of a cross-correlation calculation is dominated by the sensitivity function, which is a form of noise as described in Item 2 of Table 2. The B2B alignment map Δx(x) is explained in further in Table 2 and with reference to FIG. 5.

Alignment to Compensate for Geometric Distortion

This section describes embodiments of methodologies for alignment to compensate for geometric distortions, which may be accomplished in many ways. In the embodiment described here, geometric distortion is accommodated by decomposing the images into subregions, detecting the shifts between images in those subregions and interpolating these shifts throughout the full image.

FIG. 4 shows one of the many ways to decompose an image into subregions. Consider the alignment of two blank plate images. For example, as depicted in FIG. 3, blank plate image 1 is the base image (referred to herein as $g_1(x)$) and blank plate image 2 (referred to herein as $g_2(x)$) is aligned to it. Both of these blank plate images are decomposed into identical subregions. In Stage 1 of FIG. 4 a rigid alignment is executed, where, in this embodiment, a cross correlation is calculated according to the following expression:

$$R(x) = g_2(x) \star g_1(x) = \int_{x'} \int g_1(x')g_2(x'+x)dx' \quad (5)$$

This cross correlation will have a maximum value at the value of x that represents the spatial shift that $g_2(x)$ must undergo in order to be aligned with the base image $g_1(x)$. The location of this maximum, and thereby the shift value, may be calculated to a subpixel precision in a number of ways. Doing so, improves the effectiveness of the alignment by giving the shift vectors a subpixel precision. The two functions $g_1(x)$ and $g_2(x)$ are preconditioned prior to carrying out Equation 5. For example, to eliminate errors due to circular convolution, each of them may be multiplied by an empirically determined window function (e.g., a Gaussian function or a raised cosine function). In addition or alternatively, they may be padded, by extending their borders using one of the padding methods described in [Castleman, Sec. 9.3.4]. The outcome of this calculation is the shift value that is needed to align the two images if geometric distortion is disregarded. Modifications to this approach deal with a rotation [Wolberg; Cideciyan; DeCastro, 1987a, 1987b; O'Connor]. One of them is expressed according to the following expression:

$$R_{rot}(x, \theta) = g_{2\_rot}(x, \theta) \star g_1(x) = \int_{x'} \int g_1(x')g_{2\_rot}(x'+x, \theta)dx' \quad (6)$$

with notation defined in Table 2. The output of this operation is a 3D function that has a maximum value at a location of x,θ. This value of x,θ is the amount of shift and rotation that must be applied to $g_2(x)$ in order for it to be aligned with $g_1(x)$.

Geometric distortion is considered by applying a series of alignments. See FIGS. 4-7. FIG. 6 shows a flowchart that describes the series of alignments. The first alignment is a rigid alignment like the one described above. The outputted image that was shifted, then, is input to the next stage where another alignment is processed. In the next stage the images are decomposed into subregions. The resulting alignment may be output again and the alignment may be repeated with smaller subregions.

FIG. 5 is a depiction of the shifts in relation to the subregion boundaries and centers. The vectors that are shown as arrows are calculated at each subregion and assigned to the subregion's center. They represent the shifts that, when applied at the centers of the four subregions, cause an unaligned image to align to the base image. These shift values correspond to the center of each subregion, indicated by the dark circles. A reverse map operation is used. A reverse map operation is one where the locations indexed by x are scanned in the output (aligned) image, and at each x location the shift vector is retrieved. This shift vector is used, then, to calculate the location within the input (unaligned) image that contains the pixel value that will be moved to the x location of the output image. The values of Ax values that lay between the centers (i.e., the dark circles) are interpolated from the values that lay at the centers. This interpolation can be accomplished in many ways. Any sort of interpolation may be used, including a bilinear interpoloation or many types of spline interpolation. One of the effective interpolation schemes [Larkin; Gonzalez] involves solving the coefficients of polynomials in two sets of simultaneous equations. The first set is defined by:

$$\Delta x_{h,i} = c_{h,1}x_{h,i} + c_{h,2}x_{v,i} + c_{h,3}x_{h,i}x_{v,i} + c_{h,4}, \quad (7)$$

with notation defined in Table 2. The second set is defined by:

$$\Delta x_{v,i} = c_{v,1}x_{v,i} + c_{v,2}x_{v,i} + c_{v,3}x_{h,i}x_{v,i} + c_{v,4}, \quad (8)$$

with notation defined in Table 2. Each of these two equations represents a set of 4 simultaneous equations. Each set of equations is solvable because there are 4 equations and 4 unknowns.

There is an equation for each of the four vectors depicted in FIG. 5. The knowns are the $\Delta x_i = (\Delta x_h, \Delta x_v)$ vectors at each of the four corners shown in FIG. 5. The unknowns are the c coefficients. Considering the solution of Eq. 7, the c coefficients are solved by inserting the known values of $\Delta x_{h,i}$, $x_{h,i}$ and $x_{v,i}$ into the four simultaneous equations, each of which corresponds to the four points denoted by 1, 2, 3 and 4 in FIG. 5. The c coefficients of Equation 8 are solved in a similar way. Once these c coefficients are solved the values of $\Delta x_i = (\Delta x_{h,i}, \Delta x_{v,i})$ at any value of $x=(x_h, x_v)$ may be determined for points of x that lay within the box whose corners are defined by the black circles in FIG. 5 by calculating the right-hand-side of Equations 7 and 8 while inserting $(x_h, x_v)$ for $(x_{h,i}, x_{v,i})$.

There may be a series of alignments of this type in order to accommodate geometric distortion, as depicted in FIGS. 4 and 6. For example, consider an image dimension of 1024×1024. The first alignment in the series may have just one region, which is defined by the whole image of dimension 1024×1024. This type of alignment, which does not compensate for geometric distoration, is called a rigid alignment. It may compensate for a rotation using a number of approaches including those described in the *Alignment with Geometric Distortion* section and in [Wolberg; Cideciyan; DeCastro, 1987a, 1987b; O'Connor]. A rotation can occur when the plate is rotated from one exposure to the next. The second alignment may then input the images aligned from the first alignment and, from them, carry out another alignment using a series of 16 subregions, each having a dimension of 256×256. A third alignment may then input the images aligned from the second alignment and, from them, carry out an alignment using a series of subregions, each having a dimension of 16×16.

As noted, the term blank plate-to-blank plate (B2B) alignment map refers to a map in which blank plate images are aligned with each other.

Alignment of Blank Plate Images to Specimen Image

FIG. 8 shows a flowchart that includes an embodiment of an alignment of the merged blank plate image to the specimen image using a similar approach to that described in FIG. 3. The antipodal situation is effective as well. The antipodal situation is that where the specimen image is aligned to the blank plate image, and thereby is the one whose pixels are moved. The illustrative embodiments, however, mostly refer to the former situation. The inputted blank plate image is the merged blank plate image that is output at Stage 8 of FIG. 3. This alignment is needed because the subsequent correction step (Stage 8, FIG. 8) relies upon the phosphor grain pattern being aligned between the blank plate image and the specimen image. When a blank plate image, including a merged blank plate image, is aligned to a specimen image, the alignment map is referred to herein as a blank plate-to-specimen (B2S) alignment map. Note that the term B2S, as used herein, refers to both alignment approaches, including references to the B2S process and alignment maps.

Correction for Sensitivity Function

The sensitivity function or pattern s(x) is calculated using the merged blank plate image. Under ideal conditions the correction scheme indicated by Equation 4 is mathematically accurate to correct for the sensitivity nonuniformity represented by s(x). However, in practice it may not always be effective because s(x) can have small values that cause the division by s(x) to result in an amplification of noise in the $g_n(x)$ term. A regularization scheme is needed that prevents such noise amplification. One simple embodiment of such a scheme, patterned after the Wiener inverse filter [Castleman; Holmes, 1992b], prevents this noise amplification. The Wiener-type correction is expressed by:

$$\hat{g}(x) = g_n(x)c(x), \quad (9)$$

where:

$$c(x) = \frac{s(x)}{[s(x)]^2 + \varepsilon}. \quad (10)$$

The term ε is an empirically determined scalar that prevents the c(x) from having extremely large values when s(x) has very small values.

The computed radiography plates have a nonlinear response to x-ray exposure, so the c(x) needs to be transformed by a nonlinear operation. One approach to a nonlinear operation is expressed according to:

$$c_{nl}(x) = [c(x)]^\gamma \quad (11)$$

where terms are defined in Table 2.

It is advantageous to normalize the correction factor. Doing so will cause the average pixel value of the corrected specimen image to be roughly the same as the uncorrected specimen image, which helps the examiner to interpret the images and control the inspection procedure. The normalized correction factor is expressed as:

$$c_{nln}(x) = \frac{c_{nl}(x)}{\sum_{x' \in S_{roi}} c_{nl}(x')} \quad (12)$$

where terms are defined in Table 2.

There are other ways to apply a nonlinearity to the correction factor. Some examples are explained in Table 5.

TABLE 5

Examples of nonlinearity operators

| | Name | Expression | | Parameter(s) Optimized |
|---|---|---|---|---|
| 1. | Exponential | $c_{nl}(x) = 1 - e^{\gamma c(x)}$ | (13) | γ |
| 2. | $1^{st}$ order expansion | $c_{nl}(x) = a_0 + a_1 c(x)$ | (14) | $a_0, a_1$ |
| 3. | polynomial | $c_{nl}(x) = \sum_i a_i [c(x)]^i$ | (15) | $a_i$ |

The embodiment of equation 13 requires one nonlinearity parameter—i.e., γ. Other nonlinearity approaches, such as rows 2 and 3 in Table 5 may require more than one parameter to be optimized.

In this embodiment, the nonlinearity is optimized by solving for the value of γ that minimizes an objective function. This may be done by the scheme shown in FIG. 12, which is one of many effective ways. This scheme uses the Good's roughness measure. As noise in an image increases or decreases, respectively, the Good's roughness measure tends to increase or decrease. The Good's roughness measure is described according to [Joshi]:

$$B(\gamma) = \sum_{x \in S_{roi}} \left\{ \left[ \frac{\sqrt{\hat{g}(x_h + \Delta x_h)} - \sqrt{\hat{g}(x_h - \Delta x_h)}}{\Delta x_h} \right]^2 + \left[ \frac{\sqrt{\hat{g}(x_v + \Delta x_v)} - \sqrt{\hat{g}(x_v - \Delta x_v)}}{\Delta x_v} \right]^2 \right\} \quad (16)$$

Other measures besides Good's roughness measure may be used, including examples that are listed in Table 6.

TABLE 6

Examples of parameters that measure noise level

| Parameter | Expression for B(γ) | |
|---|---|---|
| Total variation [Dey; Rudin] | $\sum_{x \in S_{roi}} \left\{ \left[ \frac{\hat{g}(x_h + \Delta x_h) - \hat{g}(x_h - \Delta x_h)}{\Delta x_h} \right]^2 + \left[ \frac{\hat{g}(x_v + \Delta x_v) - \hat{g}(x_v - \Delta x_v)}{\Delta x_v} \right]^2 \right\}$ | (17) |

TABLE 6-continued

Examples of parameters that measure noise level

| Parameter | Expression for B(γ) | |
|---|---|---|
| Variance | $\sum_{x \in S_{roi}} [\hat{g}(x) - m_{roi}]^2$ | (18) |
| Standard deviation | $\sqrt{\sum_{x \in S_{roi}} [\hat{g}(x) - m_{roi}]^2}$ | (19) |

There are many ways to choose the region of interest over which the nonlinearity parameters are optimized. Some examples are explained in Table 7. In NDT applications the nonlinearity parameter will be most effective for a range of pixel values that are represented in the region of interest. Typically, a radiographer may be inspecting a range of material thicknesses in a specimen which correspond to the range of pixel values.

TABLE 7

Examples of ways to select the region of interest for optimizing the nonlinearity

| 1. | Manually | The user draws a box or other closed boundary that surrounds the region of interest. The user may draw the boundary around the region that is being inspected, or around a region that has a similar material thickness compared to the regions that are inspected. |
|---|---|---|
| 2. | Automatically | The software algorithm automatically segments the region of optimization based upon a range of pixel values. The user may draw a closed region around a typical portion that represents the intended material thickness range. The software then automatically segments the pixels over the whole image whose pixel values lay within a range that represents the material thickness range. |
| 3. | Whole image | The nonlinearity parameter is optimized over the whole image or around the the portion of the image where the inspected specimen resides. The user may draw a closed region around the specimen or the software may automatically segment the region of the specimen by any values that are not close to the background value. |
| 4. | Spatially adaptive | The image may be decomposed into subregions, each of which is a region where the nonlinearity parameter is optimized separately. |
| 5. | Adaptive to intensity | The image may be automatically segmented using a series of pixel value ranges as the segmentation criterion. The nonlinearity parameter is optimized, separately, for each of these ranges. The nonlinearity parameter becomes interpolated between the center pixel values of the ranges. |

The user may draw the region of interest manually. It may be convenient to draw it within a region of the image quality indicator, such as an ASTM E1025 hole type image quality indicator [ASTM Standard E1025; Halmshaw]. Doing so will ensure that the nonlinearity parameter is being optimized for the material thicknesses that the image quality indicator represents. Another way, which is equally effective, is to draw the closed region around part or all of the portion of the image that is being inspected.

A variation of this approach will automatically identify (i.e., segments) all areas in the image that have pixel values within a chosen range (chosen by percentage of the average pixel value, for example) around the average pixel value in the drawn region of interest. In this way, the nonlinearity parameters are being optimized for a range of pixel values. The automatically identified regions, then, together, represent the aggregate region of interest for optimization.

The optimization may be performed by using the whole image, or the whole portion of the image that holds the inspected specimen, as the region over which the nonlinearity parameters are optimized. This is a convenient way that ensures that the desired regions are corrected, if no specific portion of the specimen or material thickness are targeted. The trade-off is that specific narrow pixel-value ranges are not as well optimized as they could be with a more targeted region of interest.

The optimization may be made automatically spatially adaptive. The image may be decomposed automatically into regions, including a series of equally sized rectangular regions. The optimization may be carried out individually for each of these regions, so that each region has it's own nonlinearity parameter. The nonlinearity parameter may be interpolated for pixels that lay between the centers of these regions, in order to blend them and avoid edge effects.

The pixel values may be separated into ranges, with a center value and a range width. The regions of interest may then be automatically segmented using these ranges as the segmentation criteria. The nonlinearity parameter may be optimized over each of these segmented regions. The nonlinearity parameter, then, may be thought of as a function of the center value of each range. It's value may be interpolated as a function of pixel value.

Iterative Correction Schemes and Deconvolution

In one illustrative approach, an iterative scheme for correcting the specimen image based on the sensitivity function may be used. There are many ways to design an iterative scheme. Effective approaches include those that optimize an objective function using a gradient-based iterative optimization scheme. Effective choices of objective function are the I-divergence [O'Sullivan] and least-squares [Castleman] criteria, and there are many others. With an I-divergence criterion, the objective function may be expressed as:

$$L = \sum_{all x} [-\hat{g}_s(x) + g_n(x)\log\hat{g}_s(x)] \quad (20)$$

where terms are defined in Table 2. Terms may be added to this objective function that represent Lagrange multiplier terms or penalty terms for constraining properties of the estimated functions. The term $\hat{g}_s(x)$ is called the estimate of $\hat{g}_s(x)$ which is formed from estimates of the s(x) and g(x) terms in Equation 2.

Eq. 20 includes the following substitution.

$$\hat{g}_s(x) = s(x)\hat{g}(x) \quad (21)$$

Eq.'s 20 and 21 lead to an iterative algorithm that estimates g(x) and may thereby be considered an iterative correction. One approach is described here. A gradient based scheme for maximizing (i.e., optimizing) the value of L is derived by taking the gradient (i.e., partial derivative) of L respect to $\hat{g}(x)$, and arriving at the following iteration step:

$$\hat{g}(x) \leftarrow \hat{g}(x) + \alpha_g[\Delta\hat{g}(x)], \quad (22)$$

with terms defined in Table 2. The term $\Delta\hat{g}(x)$ represents iterative changes that are applied to the estimates $\hat{g}(x)$. An effective gradient-based approach to define these changes is expressed by the following equation:

$$\Delta\hat{g}(x) = w_g(x)\frac{\partial L}{\partial \hat{g}(x)} \quad (23)$$

Alternatively, Eq. 20 may include the substitution of Eq. 24, below, by substituting Eq. 1 for g(x) and placing a hat over the estimated terms:

$$\hat{g}_s(x) = s(x)\hat{g}(x) = s(x)[\hat{f}(x)*\hat{h}(x)] \quad (24)$$

Eq. 24 leads to a deconvolution algorithm according to many approaches. One approach is described here. A gradient based scheme for maximizing (i.e., optimizing) the value of L is derived by taking the gradient (i.e., partial derivative) of L respect to $\hat{f}(x)$, and arriving at the following iteration steps:

$$\hat{f}(x) \leftarrow \hat{f}(x) + \alpha_f[\Delta\hat{f}(x)], \quad (25)$$

and $$\hat{h}(x) \leftarrow \hat{h}(x) + \alpha_h[\Delta\hat{h}(x)], \quad (26)$$

with terms defined in Table 2. The terms $\Delta\hat{f}(x)$ and $\Delta\hat{h}(x)$ represent iterative changes that are applied to the estimates $\hat{f}(x)$ and $\hat{h}(x)$, respectively. An effective gradient-based approach to define these changes is expressed by the following equations:

$$\Delta\hat{f}(x) = w_f(x)\frac{\partial L}{\partial \hat{f}(x)} \quad (27)$$

$$\Delta\hat{h}(x) = w_h(x)\frac{\partial L}{\partial \hat{h}(x)} \quad (28)$$

The overrelaxation parameters $\alpha_g$, $\alpha_f$ and $\alpha_h$ are optimized to affect the largest possible change. There are many approaches to doing so. There are many other approaches to defining these iterations.

When both the image f(x) and the point spread function h(x) are estimated, this method is called a blind deconvolution [Schulz; Holmes, 1992a]. Typically, when using blind deconvolution, constraints on the properties of the two recovered signals h(x) and f(x) are needed [Schulz, 1997; Holmes 1992a]. Typical properties that can be constrained are nonnegativity, smoothness, bandlimitedness, monotonicity and support.

Effective definitions of the weighting functions $w_f(x)$ and $w_h(x)$, respectively, are $w_f(x)=\hat{f}(x)$ and $w_h(x)=\hat{h}(x)$ [Kaufman; Lewitt]. These weighting functions can speed the convergence of the algorithm. A nonlinearity may need to be applied to s(x), similar to the nonlinearity that is applied to c(x) explained in the Correction for Sensitivity Function section, in order to accommodate the nonlinear response of the sensor plate.

An embodiment of workflow steps for sensitivity function correction is shown in FIG. 9. This workflow includes the interaction of the user and the software's execution. Steps 1-3 specify the creation of all the necessary radiographs by exposing images of the specimen and the blank plate images for calibrating the sensitivity function. Steps 4-6 specify the preconditioning that is necessary to applied to the radiographs to ready them for the correction algorithm. Steps 7-9 specify the calculation of a correction factor image, including the optimization of nonlinearity parameters. Steps 10-12 complete the correction. Equation 12, and the equations leading to Equation 12 (i.e., Equations 9-11) represent an embodiment of a correction factor image, where x represents an index of the pixel of the image.

Approach 2 Merging Specimen Images

In a second approach noted above in FIG. 2, radiographs (i.e., a set of specimen images) of the same specimen may be merged to reduce noise. An effective way to do so uses frame averaging. With frame averaging, the image intensity value at each pixel location is averaged over the image set, as expressed in the following equation:

$$g_m(x) = \frac{1}{N_m}\sum_{i=1}^{N_m} g_{al,i}(x) \quad (29)$$

with notation defined in Table 2. The $g_{al,i}(x)$ are the outputs of Stage 5 in FIG. 10 that are designated as Stage 6.

This averaging operation reduces every type of noise listed in Table 3. This includes the reduction of the noise that is caused by the sensitivity function, because the fixed pattern of the sensitivity function will be randomly shifted from frame to frame so it has a random character and, in this way, behaves much like the other types of noise listed.

There are many ways to merge the images besides averaging. One way is to replace the averaging operation with the median operation. This is effective for eliminating dust, lint and other particles that settle on the computed radiography plate. When a piece of dust settles on the plate, it stays for one exposure and then is usually gone in the next exposure. Another operation involves taking the median or average at each pixel location after removing outliers. Another operation involves rank ordering the values associated with a pixel location, from the set of radiographs, and then averaging those values that are in or near the center of the rankings and that represent a chosen percentage of the rankings.

Embodiments of the work flow and algorithm for collecting the radiographs and merging the images are shown in FIG. 11. For aligning the images, algorithms that are like those described in the Alignment Method section and FIGS. 4-7 may be used. In this case, however, the phosphor grain pattern is not enhanced beforehand. The alignment is keying upon the specimen features rather than the phosphor grain pattern.

The sensitivity function correction and merger of specimen images may be carried out in concert in order to compound their noise reduction. One way of doing so is to carry out the sensitivity function correction process on each of the inputted specimen images, depicted at Stage 1 of FIG. 10, prior to inputting them.

Rigidity Device

When the merger of specimen images is applied, parallax can occur as illustrated in FIG. 13. Parallax differences among images causes errors in the interpretation of the image. It causes the merging operation to be error prone as well. The projected relative location of specimen details ($d_1$, $d_2$ and $d_3$), such as defects, move with respect to one another when examining the different image exposures. This problem occurs when the details are at different depths within the specimen. This erroneous effect is called parallax.

The orientation of the specimen to the x-ray source may be defined by its vertical and horizontal distances between the source ($h_c$ and $d_c$) and the center of the specimen. It is further defined by the angle of one of its axes with respect to an axis defined through the x-ray source ($\varphi_1$). The drawing in FIG. 13 depicts only a two dimensional abstraction of the real 3D situation. The orientation parameters could be depicted more realistically in three dimensions (FIG. 14). The importance of rotation is illustrated in FIG. 14. Parallax differences are avoided by ensuring that all of these geometric parameters ($h_c$, $d_c$, $\varphi_1$, their 3D counterparts and rotation illustrated in FIG. 14) are the same from one image exposure to the next. In simple heuristic terms, the geometric orientation between the source and the specimen must be rigid from one exposure to the next.

It is important, as well, that the relative orientation of the plane upon which the plate or cassette resides, with respect to the x-ray source and specimen, is unchanged between image exposures. The computed radiography plate position can move between exposures. It may move along any axis with respect to the table-top depicted in FIG. 15. It may rotate as well. However, it must lay in the same plane with respect to the specimen. Usage of a table as depicted in FIG. 15 will ensure this condition. Any movement of the plate, so long as its plane does not move, will be compensated by the alignments of the blank plate images.

An embodiment of the design of a device that ensures this rigidity is shown in FIG. 15. The device can be made of many materials and may be fabricated using materials that are found in many hardware stores, laboratories, offices or homes. The component labeled as the polystyrene foam block (commonly called Styrofoam®—registered trademark of Dow Chemical) needs to be rigid and must not attenuate x-rays appreciably. Other materials besides polystyrene foam may be used as long as they have these rigid and non-attenuating properties. Many types of tape, light-duty glue or hook-and-loop fasteners may be used to hold the components together. Tape is effective because it is straightforward to remove from the specimen afterwards. Open access to the plate cavity that is under the stytrofoam block is straightforward to set up, so that the plate or cassette can be easily removed and replaced between exposures. An embodiment of the work flow is explained in the following list: (1) place the cassette into the plate cavity; (2) expose the specimen to the x-rays; (3) remove the plate or cassette; (4) process the computed radiography plate with the read out unit to digitize the specimen image; (5) store the image into computer memory; (6) erase the computed radiography plate. These 5 steps are repeated for the chosen number of images to be merged. It is critical that the specimen's position, rotation and other aspects of its orientation do not move between these exposures.

In some situations, such as factories, the specimen cannot be placed below the x-ray source. It may need to be situated horizontally or over the x-ray source. By the configuration in FIG. 15, gravity holds the plate or cassette onto the plane of the table. These other situations, where gravity will not help, are accommodated by adhering the plate or cassette to the so-called table surface using many types of fasteners. Many types of tapes, hook-and-loop fasteners and other adhesives will be effective for this purpose.

If the specimen is heavy a light material such as styrofoam may not have sufficient strength to hold the specimen. FIG. 16 shows an example of a rigidity device that will hold a heavy specimen. The material of the rigidity device can be many heavy materials that are sufficiently strong to hold heavy objects. The trusses are only on the outer portions of the device, so the most of the specimen will be exposed by the x-rays without attenuation from the rigidity device. The outer portions of the specimen that overlay the trusses will experience attenuation, so measures will be required to ensure that the important portions of the specimen do not overlay the trusses. Generally, the length or width of the device need to be less than the length or width of the specimen. There are many variations on the designs shown in FIGS. 15 and 16, including those with trusses, as well as completely different designs, that will accomplish the same objective. One of the simplest designs involves placing blocks of material under the 3 or 4 far ends of the specimen. This arrangement will hold the specimen off the table and the computed radiography plate can be repeatedly placed under the specimen without moving the specimen.

Region of Interest

In further embodiment that may be applied to any of the image fidelity improvements described herein, processing of image data (blank plate images, specimen images, etc.) may be limited to a selected region of interest. A region of interest may be selected by any criterion, including manual or automated. For example, the user of the software may draw a closed region about a structure of interest to define the region of interest. Alternatively, a region of interest may be chosen automatically by a segmentation algorithm that identifies types of objects, material thickness or image intensity ranges. By doing so, the images, including the blank plate and specimen images, will be cropped to the chosen region and then the chosen operation will be applied to the cropped region. Sufficient margin in the crop operation will be needed to accommodate misalignment of the borders of the cropped regions without causing artifacts at the edges of the cropped images.

A region of interest such as this may be used for any of the image fidelity improving operations described, including the sensitivity correction, image merging and deconvolution.

The advantage of a region of interest feature is that the computation time is shortened, so the computational power requirement of the computer may be less or the user may experience faster results of the operation.

While the embodiments are generally directed to computed radiography, many of the aspects of the invention may also be applied to digital radiography and film radiography (in cases where the x-ray film image is digitized). The embodiments may be used for any number of applications including nondestructive testing, medical applications and any other application where x-ray radiography is employed.

Computing System

It is understood that image processing system 18 (FIG. 1) may be implemented as a computer program product stored on a computer readable storage medium. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Python, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Computing system 10 (FIG. 1) may comprise any type of computing device and for example includes at least one processor 12, memory 20, an input/output (I/O) 14 (e.g., one or more I/O interfaces and/or devices), and a communications pathway 16. In general, processor(s) 12 execute program code which is at least partially fixed in memory 20. While executing program code, processor(s) 12 can process data, which can result in reading and/or writing transformed data from/to memory and/or I/O 14 for further processing.

The pathway 16 provides a communications link between each of the components in computing system 10. I/O 14 can comprise one or more human I/O devices, which enable a user to interact with computing system 10. Computing system 10 may also be implemented in a distributed manner such that different components reside in different physical locations.

Furthermore, it is understood that the image processing system 18 or relevant components thereof (such as an API component, agents, etc.) may also be automatically or semi-automatically deployed into a computer system by sending the components to a central server or a group of central servers. The components are then downloaded into a target computer that will execute the components. The components are then either detached to a directory or loaded into a directory that executes a program that detaches the components into a directory. Another alternative is to send the components directly to a directory on a client computer hard drive. When there are proxy servers, the process will select the proxy server code, determine on which computers to place the proxy servers' code, transmit the proxy server code, then install the proxy server code on the proxy computer. The components will be transmitted to the proxy server and then it will be stored on the proxy server.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

The invention claimed is:

1. A method of processing a computed radiographic specimen image to generate an enhanced specimen image, comprising:
   determining a sensitivity function of a computed radiography (CR) plate from at least one blank plate image, wherein the sensitivity function is a measure of noise caused by a phosphor grain pattern in the CR plate;
   inputting a specimen image captured using the CR plate;
   generating a blank plate-to-specimen (B2S) alignment map that provides a correspondence between pixel locations in the sensitivity function and the specimen image;
   aligning the sensitivity function to the specimen image;
   applying a sensitivity function correction algorithm to the specimen image based on the aligned sensitivity function, wherein the sensitivity function correction algorithm is derived from the sensitivity function; and
   outputting an enhanced specimen image.

2. The method of claim 1, wherein the sensitivity function correction algorithm utilizes an iterative process.

3. The method of claim 1, wherein the sensitivity function correction algorithm includes calculating a correction-factor image that is applied to the specimen image.

4. The method of claim 3, wherein the correction-factor image uses a regularization scheme to prevent nose enhancement.

5. The method of claim 3, wherein a nonlinearity is applied to the correction-factor image.

6. The method of claim 5, wherein at least one nonlinearity parameter is optimized automatically using an objective criterion designed to minimize noise.

7. The method of claim 6, wherein the at least one nonlinearity parameter is optimized automatically and adaptively at a variety of spatial locations in the specimen image.

8. The method of claim 1, wherein processing of at least one blank plate image and specimen image is limited to a manually or automatically chosen region of interest.

9. The method of claim 1, wherein determining the sensitivity function includes aligning independent blank plate images to one another without fiduciary marks.

10. The method of claim 1, wherein deconvolution is utilized.

11. The method of claim 10, wherein the deconvolution is applied iteratively.

12. The method of claim 10, wherein the deconvolution is applied to a manually or automatically chosen region of interest.

13. The method of claim 1, wherein the B2S alignment map is used to spatially align the phosphor grain pattern in at least one blank plate image to the phosphor grain pattern in the specimen image without fiduciary marks.

14. The method of claim 1, wherein the B2S alignment map is determined with a cross correlation calculation.

15. The method of claim 1, wherein the B2S alignment map is determined with a cross correlation calculation.

16. The method of claim 1, wherein a merged blank plate image is generated from a plurality of blank plate images in which:
   a plurality of blank plate-to-blank plate (B2B) alignment maps are calculated;
   the plurality of B2B alignment maps are used to generated a set of aligned blank plate images; and
   the aligned blank plate images are merged.

17. The method of claim 16, wherein the phosphor grain pattern in each blank plate image is enhanced to improve the plurality of B2B alignment maps.

18. The method of claim 15, wherein a spatially varying geometric distortion is utilized in the plurality of B2B alignment maps.

19. A computer system for enhancing computed radiographic images, comprising:
   a system for determining a sensitivity function of computed radiography (CR) plate from at least one blank image, wherein the sensitivity function is a measure of noise caused by a phosphor grain pattern in the CR plate;
   a system for generating a blank plate-to-specimen (B2S) alignment map that provides a correspondence between pixel locations in the sensitivity function and a specimen image captured with the CR plate; and
   a system for generating an enhanced specimen image by applying a correction algorithm to the specimen image using the B2S alignment map, wherein the correction algorithm is derived from the sensitivity function.

20. The system of claim 19, wherein the sensitivity function is determined by merging a plurality of blank plate images.

21. The system of claim 20, wherein merging the set of blank plate images includes:
   calculating a plurality of blank plate-to-blank plate (B2B) alignment maps;
   generating a set of aligned blank plate images using the plurality of B2B alignment maps; and
   merging the aligned blank plate images.

22. A computer program product stored on a computer readable medium, which when executed by a computing system, enhances computed radiographic images, comprising:
   program code for determining a sensitivity function of a computed radiography (CR) plate from at least one blank plate image, wherein the sensitivity function is a measure of noise caused by a phosphor grain pattern in the CR plate;

program code for generating a blank plate-to-specimen (B2S) alignment map that provides a correspondence between pixel locations in the sensitivity function and a specimen image captured with the CR plate; and program code for generating an enhanced specimen image by applying a correction algorithm to the specimen image using the B2S alignment map, wherein the correction algorithm is derived from the sensitivity function.

23. The computer program product of claim 22, wherein the sensitivity function is determined by merging a plurality of blank plate images.

24. The computer program product of claim 23, wherein merging the set of blank plate images includes:

calculating a plurality of blank plate-to-blank plate (B2B) alignment maps;

generating a set of aligned blank plate images using the plurality of B2B alignment maps; and merging the aligned blank plate images.

25. A method of processing a computed radiographic specimen image to generate an enhanced specimen image, comprising:

inputting a blank plate image captured using a computed radiography (CR) plate;

inputting a specimen image using the CR plate;

calculating spatial misalignments between the specimen image and the blank plate image by analyzing similarities in phosphor grain patterns between the specimen image and the blank plate image;

generating an enhanced image the compensates for a spatially varying sensitivity of the CR plate based on the spatial misalignments; and outputting the enhanced specimen image.

26. A method of processing a computed radiographic specimen image to generate an enhanced specimen image, comprising:

inputting a plurality of blank plate images using a CR plate; and calculating first spatial misalignments among the plurality of blank plate images by analyzing similarities in phosphor grain patterns of the blank page images;

inputting a specimen image using the CR plate;

calculating second spatial misalignments between the specimen image and the blank plate images by analyzing similarities in phosphor grain patterns between the specimen image and the blank plate images;

generating an enhanced image that compensates for a spatially varying sensitivity of the CR plate based on the second spatial misalignments; and outputting the enhanced specimen image.

27. The method of claim 26, wherein calculating the first spatial misalignments includes merging the blank plate images into a merged blank plate image.

28. The method of claim 27, wherein the blank plate images used to calculate the second spatial misalignments comprise the merged blank plate image.

* * * * *